(12) United States Patent
Alexander et al.

(10) Patent No.: US 11,744,573 B2
(45) Date of Patent: Sep. 5, 2023

(54) DEVICES AND METHODS FOR LOCATING AND IMPLANTING TISSUE ANCHORS AT MITRAL VALVE COMMISSURE

(71) Applicant: Edwards Lifesciences Corporation, Irvine, CA (US)

(72) Inventors: John Alexander, Pinehurst, NC (US); Megan E. Holmes, Nashua, NH (US); Richard D. Hudson, Seabrook, NH (US); Christopher C. Lee, Tweksbury, MA (US); Steven D. Cahalane, Pelham, NH (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 202 days.

(21) Appl. No.: 17/173,883

(22) Filed: Feb. 11, 2021

(65) Prior Publication Data

US 2021/0161520 A1 Jun. 3, 2021

Related U.S. Application Data

(60) Continuation of application No. 16/123,759, filed on Sep. 6, 2018, now Pat. No. 10,918,373, which is a
(Continued)

(51) Int. Cl.
*A61F 2/24* (2006.01)
*A61B 17/04* (2006.01)
(Continued)

(52) U.S. Cl.
CPC ...... *A61B 17/0401* (2013.01); *A61B 18/1492* (2013.01); *A61B 2017/003* (2013.01);
(Continued)

(58) Field of Classification Search
CPC ...... A61B 17/0401; A61B 2017/00243; A61B 2090/3966; A61F 2/2466
See application file for complete search history.

(56) References Cited

U.S. PATENT DOCUMENTS

| 3,604,488 A | 9/1971 | Wishart et al. |
|---|---|---|
| 3,656,185 A | 4/1972 | Carpentier |

(Continued)

FOREIGN PATENT DOCUMENTS

| CN | 113331995 A | 9/2021 |
|---|---|---|
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Alexander J Orkin
(74) *Attorney, Agent, or Firm* — Thomas C. Richardson

(57) ABSTRACT

A system is transluminally advanced into the heart of a subject. A first portion of the system is positioned through a native valve of the heart, the system including wires disposed at the first portion. The first portion is stabilized at the native valve by positioning a distal portion of the system within a blood vessel of the subject. While the distal portion of the system remains within the blood vessel, the wires are induced to bow laterally such that the wires press against the native valve. While the wires remain pressed against the native valve, the shape of the wires is radiographically imaged. An anchor is transluminally anchored to tissue of the native valve, facilitated by the imaging. Other embodiments are also described.

31 Claims, 14 Drawing Sheets

Related U.S. Application Data division of application No. 14/472,867, filed on Aug. 29, 2014, now Pat. No. 10,070,857.

(60) Provisional application No. 61/872,704, filed on Aug. 31, 2013.

(51) Int. Cl.
- *A61B 18/14* (2006.01)
- *A61B 17/00* (2006.01)
- *A61B 17/22* (2006.01)
- *A61B 90/00* (2016.01)

(52) U.S. Cl.
CPC .............. *A61B 2017/00243* (2013.01); *A61B 2017/00783* (2013.01); *A61B 2017/0406* (2013.01); *A61B 2017/0409* (2013.01); *A61B 2017/22044* (2013.01); *A61B 2017/22047* (2013.01); *A61B 2090/3966* (2016.02); *A61F 2/243* (2013.01); *A61F 2/2466* (2013.01); *A61F 2/2496* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donion et al. |
| 6,652,556 B1 | 11/2003 | VanTassel et al. |
| 6,682,558 B2 | 1/2004 | Tu et al. |

(56) References Cited

U.S. PATENT DOCUMENTS

| | | |
|---|---|---|
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |

(56) References Cited

U.S. PATENT DOCUMENTS

| | | |
|---|---|---|
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,968,335 B2 | 3/2015 | Robinson et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |

(56) References Cited

U.S. PATENT DOCUMENTS

| | | |
|---|---|---|
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0173300 A1 | 8/2006 | Oslund et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |

(56) References Cited

U.S. PATENT DOCUMENTS

| | | |
|---|---|---|
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0183194 A1 | 7/2008 | Goldfarb et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228265 A1 | 9/2008 | Spence et al. |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |

(56) References Cited

U.S. PATENT DOCUMENTS

| | | |
|---|---|---|
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0261655 A1 | 10/2013 | Drasler et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |

(56) References Cited

FOREIGN PATENT DOCUMENTS

| | | |
|---|---|---|
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannessen. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The double orifice technique in mitral valve repair: a simple solution for complex problems," Journal of Thoracic Cardiovacular Surgery 122:674-681 (2001).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgicai Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An Implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978, An improved mechanical device for control of urinary incontinence. Investigative urology, 15(5), pp. 389-391.

Swenson, Orvar, "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

DEVICES AND METHODS FOR LOCATING AND IMPLANTING TISSUE ANCHORS AT MITRAL VALVE COMMISSURE

CROSS-REFERENCE TO RELATED APPLICATIONS

The present application is a Continuation of U.S. patent application Ser. No. 16/123,759 to Alexander et al., filed Sep. 6, 2018, which is a Divisional of U.S. patent application Ser. No. 14/472,867, to Alexander et al., filed Aug. 29, 2014 (now U.S. Pat. No. 10,070,857), which is based on and claims priority to U.S. Provisional Patent Application 61/872,704 to Alexander et al., filed, Aug. 31, 2013, all of which are incorporated by reference, as if expressly set forth in their respective entireties herein.

TECHNICAL FIELD

The present teachings generally relate to a delivery catheter system that is adapted to deliver multiple devices, such as guide wires, across the commissure of the mitral valve annulus. The present teachings further relate to implanting a first tissue anchor across the commissure of the mitral annulus. Other embodiments of the present teachings relate to pulling a ventricular free wall towards a septum.

BACKGROUND

The left side of a human heart includes the left atrium (LA) and the left ventricle. The aorta receives oxygenated blood from the left ventricle through the aortic valve, which serves to prevent regurgitation of blood back into the left ventricle. The mitral valve is positioned between the left atrium and the left ventricle and allows a one-way flow of the oxygenated blood from the left atrium to the left ventricle.

The mitral valve, which will be described below in greater detail, includes an anterior leaflet and a posterior leaflet that are coupled to the chordae tendineae. The commissures define an area where the anterior and posterior leaflets join and extend into the annulus. The chordae tendineae serve as "tension members" that prevent the leaflets of the mitral valve from moving past their dosing point and prolapsing back into the left atrium. When the left ventricle contracts during a systole, the chordae tendineae prevent the upward motion (toward the left atrium) of the anterior and posterior leaflets from passing the point where the anterior and posterior leaflets meet and seal to prevent backflow from the left ventricle to the left atrium ("mitral regurgitation" or "mitral insufficiency"). The chordae tendineae arise from the columnae carneae or, more specifically, the musculi papillares (papillary muscles) of the columnae carneae. In various figures herein, some anatomical features have been deleted solely for clarity.

The anterior leaflet and the posterior leaflet of the mitral valve are generally thin, flexible membranes. When the mitral valve is closed, the anterior leaflet and the posterior leaflet are generally aligned and contact each other along a "line of coaptation" several millimeters from their free edges to create a seal that prevents mitral regurgitation. Alternatively, when the mitral valve is opened, blood flows downwardly into the left ventricle through an opening created between the anterior leaflet and the posterior leaflet.

Many problems relating to the mitral valve may cause many types of ailments. Such problems include, but are not limited to, mitral regurgitations. A mitral regurgitation, or leakage, is the backflow of blood from the left ventricle into the left atrium due to an imperfect closure of the mitral valve. Leakage often occurs when the anterior and posterior leaflets do not seal against each other, resulting in a mitral orifice between the anterior leaflet and the posterior leaflet when the leaflets are supposed to be fully coapted during a systole.

In general, a relatively significant systolic mitral orifice may exist between the anterior leaflet and the posterior leaflet for a variety of reasons. For example, a mitral orifice may exist due to congenital malformations because of ischemic disease or the heart having been damaged by a previous heart attack. Such a mitral orifice may also be treated in a congestive heart failure, e.g., cardiomyopathy or some other type of distress which causes a heart to be enlarged. Enlargement of the heart can result in dilation (stretching) of the mitral annulus. This enlargement is usually limited to the posterior valve annulus and is associated with the posterior leaflet because the anterior annulus is a relatively rigid fibrous structure. When the posterior annulus enlarges, it causes the posterior leaflet to move away from the anterior leaflet, causing a mitral orifice during systoles because the two leaflets no longer form a proper coaptation. This results in leakage of blood through the valve or regurgitation.

The blood leakage through the mitral valve generally causes a heart to operate less efficiently because the heart pumps blood both out to the body via the aorta and back (in the form of mitral regurgitation) into the left atrium. Leakage through the mitral valve, or general mitral insufficiency, is thus often considered to be a precursor to congestive heart failures (CHF) or a cause to progressively worsening of a heart failure. There are generally different levels of symptoms associated with a heart failure. These levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort and has symptoms of cardiac insufficiency even at rest. In general, correcting or reducing the degree of mitral valve leakage can reduce a patient's NYHA grade. For instance, a patient with a Class 4 classification may have his classification reduced to Class 3 or Class 2 and, as a result, the patient becomes relatively comfortable at rest or even during a mild physical exertion. By eliminating the backflow of blood into the left atrium, therapies that reduce mitral insufficiency reduce the workload of the heart and may prevent or slow the degradation of heart function and congestive heart failure symptoms that are common when a significant degree of mitral insufficiency remains uncorrected.

Treatments used to correct for mitral valve leakage or, more generally, CHF, are typically highly invasive, open-heart surgical procedures. In extreme cases, this may include implantation of a ventricular assist device such as an artificial heart in a patient with a failing heart. The implantation of a ventricular assist device is often expensive, and a patient with a ventricular assist device must be placed on an extended anti-coagulant therapy. An anti-coagulant therapy reduces the risk of blood clot formation, for example, within the ventricular assist device. Reducing the risks of blood clots associated with the ventricular assist device is desirable, but anti-coagulant therapies may increase the risk of uncontrollable bleeding in a patient, e.g., as a result of a fall.

Rather than implanting a ventricular assist device, bi-ventricular pacing devices similar to pacemakers may be implanted in some cases, including those where a heart beats inefficiently in a particular asynchronous manner. While the implantation of a bi-ventricular pacing device may be effective, not all heart patients are suitable for receiving a bi-ventricular pacing device. Further, the implantation of a bi-ventricular pacing device is expensive, and is generally not effective in significantly reducing or eliminating the degree of mitral regurgitation.

Open-heart surgical procedures that are intended to correct a mitral valve leakage, specifically, can involve the implantation of a replacement valve. Valves from animals, e.g., pigs, may be used to replace a mitral valve in a human. While a pig valve may relatively successfully replace a mitral valve, such replacement valves generally wear out, thereby requiring additional open surgeries at later dates. Mechanical valves, which are less likely to wear out may also be used to replace a leaking mitral valve. However, when a mechanical valve is implanted, there is an increased risk of thromboembolism and, as a result, the patient is generally required to undergo extended anti-coagulant therapies.

A less invasive surgical procedure involves a heart bypass surgery through a port access procedure. For a port access procedure, the heart may be accessed by cutting between ribs or sometimes removing parts of one or more ribs, as opposed to dividing the sternum and opening the entire chest of a patient in an open-heart surgery.

One open-heart surgical procedure that is particularly successful in correcting a mitral valve leakage and mitral regurgitation is an annuloplasty procedure. During an annuloplasty procedure, a medical device such as an annuloplasty ring may be implanted surgically on the left atrial side of the mitral annulus (i.e., the base of the mitral valve to the heart). The device reduces a dilated mitral valve annulus to a relatively normal size, moves the posterior leaflet closer to the anterior leaflet to aid anterior-posterior leaflet coaptation, and improves the quality of mitral valve closures during systoles. Annuloplasty rings are often shaped substantially like the letter "D" to correspond to the natural shape of the mitral annulus as viewed from above. Typically, the rings are formed from a rod or tube of a biocompatible material, including a plastic that has a DACRON mesh covering.

In order for an annuloplasty ring to be implanted a surgeon surgically attaches the annuloplasty ring to the mitral valve on its atrial side. Conventional methods for installing a ring require an open-heart surgery which involves opening a patient's sternum and placing the patient on a heart-bypass machine. The annuloplasty ring is sewn on the top portion of the mitral valve. In sewing the annuloplasty ring onto the mitral valve, a surgeon generally sews the straight side of the "D" to the fibrous tissue located at the junction between the posterior wall of the aorta and the base of the anterior mitral valve leaflet. As the curved part of the ring is sewn to the posterior aspect of the annulus, the surgeon alternately acquires a relatively larger amount of tissue from the mitral annulus, e.g., a one-eighth inch bite of tissue, using a needle and thread, compared to a relatively smaller bite taken of the fabric covering of the annuloplasty ring. After the thread has loosely coupled the annuloplasty ring to the mitral valve annulus tissue, the annuloplasty ring is slid into contact with the mitral annulus. The tissue of the posterior mitral annulus that was previously stretched out, e.g., due to an enlarged heart, is effectively reduced in circumference and pulled forwards towards the anterior mitral leaflet by the tension applied by annuloplasty ring with the suture or thread. As a result, a mitral orifice between the anterior leaflet and the posterior leaflet may be reduced and even substantially closed off during a ventricular contraction or systole in many cases, thereby significantly reducing or even eliminating mitral insufficiency. After the mitral valve is shaped by the ring, the anterior and posterior leaflets will reform typically by pulling the posterior leaflet forward to properly meet the anterior leaflet and create a new contact line that will enable the mitral valve to function properly.

Although a patient that receives an annuloplasty ring may be subjected to anti-coagulant therapies, the patient is only subjected to the therapies for a matter of weeks, e.g., until tissue grows over the annuloplasty ring.

Another type of procedure that is generally effective in reducing mitral valve leakage associated with purpose of the valve leaflets involves placing a single edge-to-edge suture in the mitral valve. For example, in an Alfieri stitch or a bow-tie repair procedure, an edge-to-edge stitch is made approximately at the center of the mitral orifice between an anterior leaflet and a posterior leaflet of a mitral valve. Once the stitch is in place between the anterior and posterior leaflets, it is pulled in to form a suture which holds the anterior leaflet against the posterior leaflet.

Another surgical procedure that reduces mitral valve leakage involves placing sutures along a mitral valve annulus around the posterior leaflet these sutures may be formed as a double track, e.g., in two "rows" from a single strand of suture material. The sutures are tied off approximately at a central point of the posterior leaflet. Pledgets are often positioned under selected sutures to prevent the sutures from tearing through the annulus. When the sutures are tightened and tied on the circumference of the annulus may effectively be reduced to a desired size such that the size of a systolic mitral orifice between the posterior leaflet and the anterior leaflet may be reduced.

While the invasive surgical procedures have proven to be effective in the treatment of mitral valve leakage, they often have significant drawbacks. Any time a patient undergoes an open heart surgery, there are risks of infection. Opening the sternum and using a cardiopulmonary bypass machine has also been shown to result in a significant incidence of both short and long term neurological deficits. Further, given the complexity of an open-heart surgery and the significant recovery time, people that are not greatly inconvenienced by CHF symptoms, e.g., people at a Class 1 classification, may choose not to have any corrective surgery. In addition, people that need an open heart surgery the most, e.g., people at a Class 4 classification, may either be too frail or too weak to undergo the surgery. Hence, many people that may benefit from a surgically repaired mitral valve may not undergo surgeries.

Alternatively, in a minimally invasive method, by using a catheter system, a cinching device with distal, mid, and proximal anchors is placed within the lumen of the CS to allow plication of the annulus via the CS. In practice, these anchors are cinched together and the distance between them is shortened by pulling a flexible tensile member such as a cable or suture. As a result, the valve annulus is shortened and the posterior leaflet is pulled closer to the anterior leaflet in a manner similar to an annuloplasty procedure. Unfortunately, since the tissue that forms the CS is relatively delicate, the anchors are prone to tear the tissue during the cinching procedure. In addition, the effect on the mitral annulus may be reduced when the CS of a particular patient is not directly aligned with the mitral annulus. Other minimally invasive techniques have been proposed but have various drawbacks related to such factors as effectiveness and/or accuracy of a catheter-based implementation.

Catheter-based surgical procedures have been used to repair a defective mitral valve. Specifically, anchors are secured at a plurality of locations around the annulus near the posterior leaflet of a mitral valve. Each anchor has a suture coupled thereto. The sutures are collectively gathered and pulled tight. As the sutures are pulled, the tissue between each pair of the adjacent anchors is plicated, thereby shortening the length of the annulus and drawing the posterior leaflet toward the anterior leaflet. Similar techniques can also be used to repair a defective tricuspid valve.

During a surgical procedure, anchors are usually introduced and seemed sequentially. A typical repair by using the catheter based surgical procedure includes one or more steps selected from introducing a catheter to a proximity of the annulus, making an incision at the annulus, introducing a guide wire through the incision site, withdrawing the catheter, introducing an anchor by tracking a second catheter through the guide wire, securing the anchor in the annulus, and withdrawing the second catheter. This procedure is repeated to secure a second anchor.

Catheters capable of delivering multiple guide wires or anchors have been disclosed. Without claiming to have exhaustively examined prior art references and without attempting to characterize any prior art reference, U.S. Patent Application Publication No. 2008-0228265 discloses a triple lumen catheter. However, distances between two of the three lumens are usually fixed. In addition, during a deployment, the two outer catheters are generally advanced lengthwise as well as laterally. In certain instances, one or both of the two outer catheters are caught by the chordae tendineae during a deployment.

There generally exists a need for an improved catheter to simplify the catheter-based mitral valve correction.

SUMMARY

One aspect of the present teachings provides a device for percutaneously locating the mitral valve commissure. In various embodiments, the device comprises a bow catheter, a central catheter, and two bow wires. In various embodiments, the bow catheter has a proximal end, a distal end, and an elongated tubular body. In various embodiments, the central catheter also has a proximal end, a distal end, and an elongated tubular body, wherein the central catheter slidably is disposed within a lumen of the bow catheter. And in some embodiments, two bow wires each has a proximal end attaching to the distal end of the bow catheter and a distal end attaching to the distal end of the central catheter. In some embodiments, as the distal ends of the bow catheter and central catheter come closer to each other, the two bow wires bend radially outward, forming a general plane.

Another aspect of the present teachings provides a device for percutaneously implanting a wire across the mitral annulus at the mitral valve commissure. In various embodiments, this device comprises a bow catheter, a central catheter, two bow wires, and at least one wire delivery catheter. In some embodiments, the bow catheter has a proximal end, a distal end, and an elongated tubular body. In some embodiments, the central catheter also has a proximal end, a distal end, and an elongated tubular body, wherein the central catheter slidably is disposed within a lumen of the bow catheter. In some embodiments, the two bow wires each has a proximal end attaching to the distal end of the bow catheter and a distal end attaching to the distal end of the central catheter. In some embodiments, as the distal ends of the bow catheter and central catheter come closer to each other, the two bow wires bend radially outward forming a general plane. In some embodiments, the at least one wire delivery catheter has a distal portion attaching to a portion of one of the two bow wire. In some embodiments, as the two bow wires bend radially outward, the distal portion of the wire delivery catheter is directed to pivot outward radially from an elongated axis of the wire delivery catheter.

Another aspect of the present teachings provides a method for percutaneously locating a mitral valve commissure. In various embodiments, the method comprises providing a mitral valve commissure locating system. In some embodiments, the mitral valve commissure locating system comprises a bow catheter having a proximal end, a distal end, and an elongated tubular body; a central catheter having a proximal end, a distal end, and an elongated tubular body; and two bow wires with proximal ends and distal ends. In some embodiments, the central catheter slidably is disposed within a lumen of the bow catheter. In some embodiments, the proximal ends of the bow wire attach to the distal end of the bow catheter and the distal ends of the bow wire attach to the distal end of the central catheter. And in some embodiments, as the distal ends of the bow catheter and central catheter come closer to each other, the two bow wires bend radially outward to form a general plane. In various embodiments, the method also comprises delivering the mitral valve commissure locating system percutaneously across the mitral valve with the distal ends of the bow wires distal to the mitral annulus and the proximal ends of the bow wires proximal to the mitral annulus. In various embodiments, the method comprises rendering the distal end of the bow catheter and the distal end of the central catheter closer to each other and the two bow wires bending radically outward. In some embodiments, the method also comprises visualizing the curvature of the bow wires as it keeps bending radially outward and discontinuing outward bending of the bow wires when a narrower waist forms along the curvature of the bow wires.

Another aspect of the present teachings provides a method for percutaneously implanting a wire across the mitral annulus at the mitral valve commissure. In various embodiments, the method comprises providing a mitral valve commissure locating system and at least one wire delivery catheter attaching to the mitral valve commissure locating system. In various embodiments, the mitral valve commissure locating system comprises a bow catheter comprising a proximal end, a distal end, and an elongated tubular body; a central catheter comprising a proximal end, a distal end, and an elongated tubular body; and two bow wires each comprising a proximal end and a distal end. In some embodiments, the central catheter slidably is disposed within a lumen of the bow catheter. In some embodiments, the proximal ends of the bow wire attach to the distal end of the bow catheter and the distal ends of the bow wire attach to the distal end of the central catheter. And as the distal ends of the bow catheter and central catheter come closer to each other, the two bow wires bend radially outward and form a general plane. In certain embodiments, the at least one wire delivery catheter comprises a distal portion attaching to a portion of one of the two bow wire. In certain embodiments, as the two bow wires bend radially outward, the distal portion of the wire delivery catheter is directed to pivot outward radially from an elongated axis of the wire delivery catheter. In various embodiments, the method comprises delivering the mitral valve commissure locating system percutaneously across the mitral valve, with the distal ends of the bow wires distal to the mitral annulus and the proximal ends of the bow wires proximal to the mitral annulus. In some embodiments, the method comprises rendering the distal end of the bow catheter and the distal end of the central catheter closer to each other and the two bow wires bending radially outward. In some embodiments, the method comprises visualizing the curvature of the bow wires as they keep bending radially outward, and discontinuing outward bending of the bow wires when a narrower waist forms along the curvature of the bow wires. In some embodiments, the method comprises positioning a distal end of the wire delivery catheter proximally and adjacent to the mitral annulus, and advancing a wire distally through the lumen of the wire delivery catheter across the mitral annulus.

DETAILED DESCRIPTION OF CERTAIN EMBODIMENTS

Figure 1A:
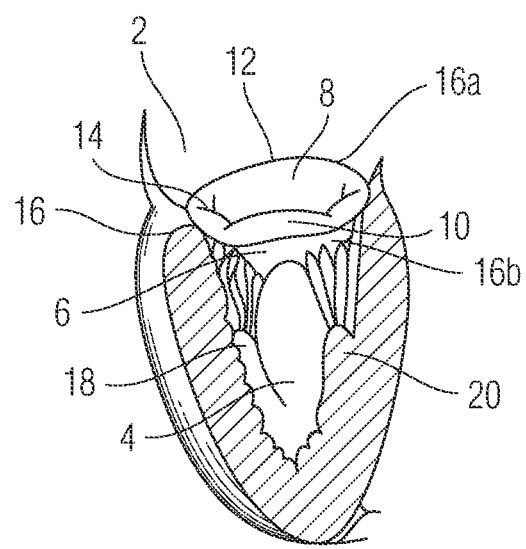
FIGS. 1a-1b illustrate the anatomy of a left heart.

Certain specific details are set forth in the following description and Figures to provide an understanding of various embodiments of the present teachings. Those of ordinary skill in the relevant art will understand that they can practice other embodiments of the present teachings without one or more of the details described herein. Thus, it is not the intention of the Applicants to restrict or in any way limit the scope of the appended claims to such details. While various processes are described with reference to steps and sequences in the following disclosure, the steps and sequences of steps should not be taken as required to practice all embodiments of the present teachings. Thus, it is not the intention of the Applicants to restrict or in any way limit the scope of the appended claims to such steps or sequences of steps.

As used herein, the terms "subject" and "patient" refer to an animal, such as a mammal, including livestock, pets, and preferably a human. Specific examples of "subjects" and "patients" include, but are not limited to, individuals requiring medical assistance and, in particular, requiring treatment for symptoms of a heart failure.

As used herein, the term "lumen" means a canal, duct, generally tubular space or cavity in the body of a subject including veins, arteries, blood vessels, capillaries, intestines, and the like. The term "lumen" can also refer to a tubular space in a catheter, a sheath, or the like in a device.

As used herein, the term "proximal" means close to the operator (less into the body) and "distal" shall mean away from the operator (further into the body). In positioning a medical device from a downstream access point, distal is more upstream and proximal is more downstream.

As used herein, the term "catheter" or "sheath" encompasses any hollow instrument capable of penetrating a body tissue or interstitial cavities and providing a conduit for selectively injecting a solution or gas. The term "catheter" or "sheath" is also intended to encompass any elongate body capable of serving as a conduit for one or more of the ablation, expandable or sensing elements. Specifically, in the context of coaxial instruments, the term "catheter" or "sheath" can encompass either the outer catheter body or sheath or other instruments that can be introduced through such a sheath. The use of the term "catheter" should not be construed as meaning only a single instrument but rather is used to encompass both singular and plural instruments, including coaxial, nested, and other tandem arrangements. Moreover, the terms "sheath" or "catheter" are sometime used interchangeably to describe catheters having at least one lumen through which instruments or treatment modalities can pass.

Unless otherwise specified, all numbers expressing quantities, measurements, and other properties or parameters used in the specification and claims are to be understood as being modified in all instances by the term "about". Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

An aspect of the present teachings provides a positioning catheter system deploys across the mitral orifice between the anterior and posterior leaflets, making out two mitral valve commissures. In various embodiments, the positioning catheter system includes a central catheter, a guide wire, and a bow catheter with two bow wires. In various embodiments upon deployment, at least one of the two bow wires bends radially outward, along the slit opening of the mitral orifice until it reaches the commissure.

Another aspect of the present teachings provides a delivery catheter system for delivering multiple wires across the mitral annulus at the mitral valve commissure. In various embodiments, the delivery catheter system comprises a positioning catheter system. In some embodiments, a wire delivery catheter tracks along the positioning catheter system and deploys a wire across the mitral annulus at the mitral valve commissure, in other embodiments, the delivery catheter system includes two wire delivery catheters each tracking along the bow wire and reaching the mitral valve commissure. In some embodiments, each wire delivery catheter independently deploys one wire across the mitral annulus at the mitral valve commissure.

Another aspect of the present teachings provides a method of plicating mitral annulus tissue around the mitral valve commissure. Upon deploying wire across the mitral annulus at the mitral valve commissure, another aspect of the present teachings further discloses implanting two tissue anchors across the annulus at the mitral valve commissure with a pre-defined distance in between. The present teachings further disclose reducing the distance between the two tissue anchors, thereby plicating the annulus tissues.

The following description refers to FIGS. 1 to 12. A person with ordinary skill in the art would understand that the figures and description thereto refer to various embodiments of the present teachings and, unless indicated otherwise by their contexts, do not limit the scope of the attached claims.

Figure 1B:
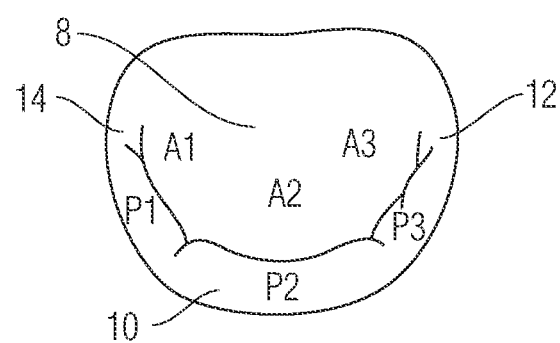

FIGS. 1a-b illustrate a mitral valve (6) between the left atrium (2) and the left ventricle (4) of the heart. Mitral valve (6) includes an anterior leaflet (8) and a posterior leaflet (10) that converge at the posteromedial commissure (12) and the anterolateral commissures (14). The semi-circular anterior leaflet (8) is anchored anteriorly to one third of the mitral annulus (16a) and the quadrangular posterior leaflet (10) is attached posteriorly to the remaining two thirds of the posterior mitral annulus (16b). The posterior leaflet (10) has two indentations, dividing the posterior leaflet into a lateral P1 scallop close to the anterolateral commissure (14), a larger central P2 scallop, and a medial P3 scallop close to the posteromedial commissure (12). Arbitrarily opposing segments of the anterior leaflet (8) are called A1; A2, and A3 scallops, respectively.

The normal anterior and posterior leaflets (8, 10) close (coapt) from their lateral to medial portions (coaptation line) during a systole, preventing blood from back flowing into the left atrium (2). The opening between the anterior and posterior leaflets (8, 10) is surrounded by a fibrous ring known as the mitral annulus (16), which resides in the left atrio-ventricular groove. The mitral annulus (16) consists of an anterior part (16a) and a posterior part (16b).

There are two papillary muscles (18, 20) arising from the area between the apical and middle thirds of the left ventricular wall, the anterolateral papillary muscles (18) and the posteromedial papillary muscle (20). Several dozens of tendinous chords (22) originate from these papillary muscles (18, 20) and attach to the ipsilateral half of the anterior and posterior mitral leaflets (8, 10).

Figure 2A:
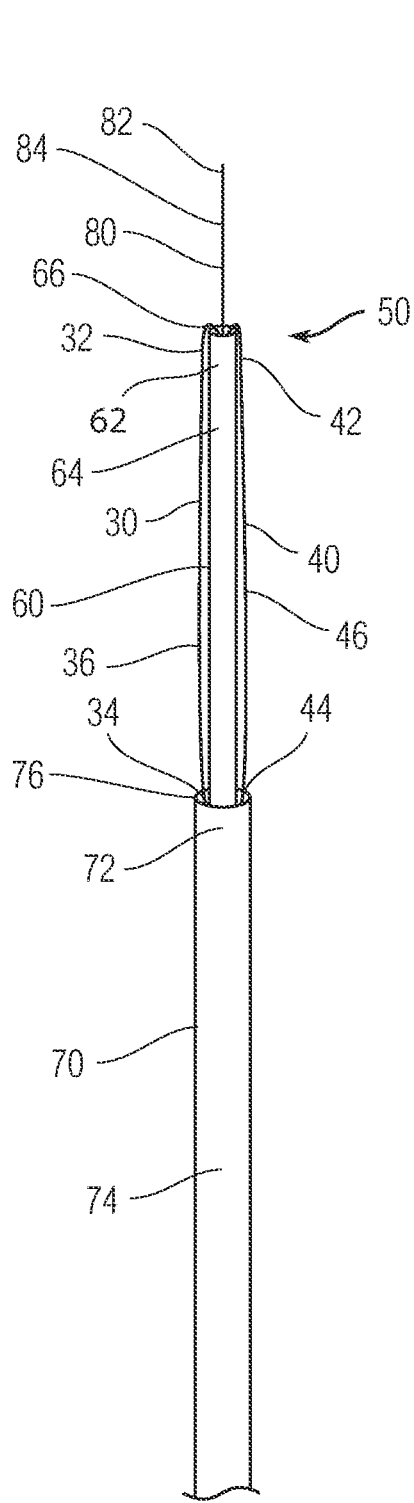
FIGS. 2a-2b are perspective views of an exemplary mitral commissure locating system in accordance with the present teachings.
Figure 2B:
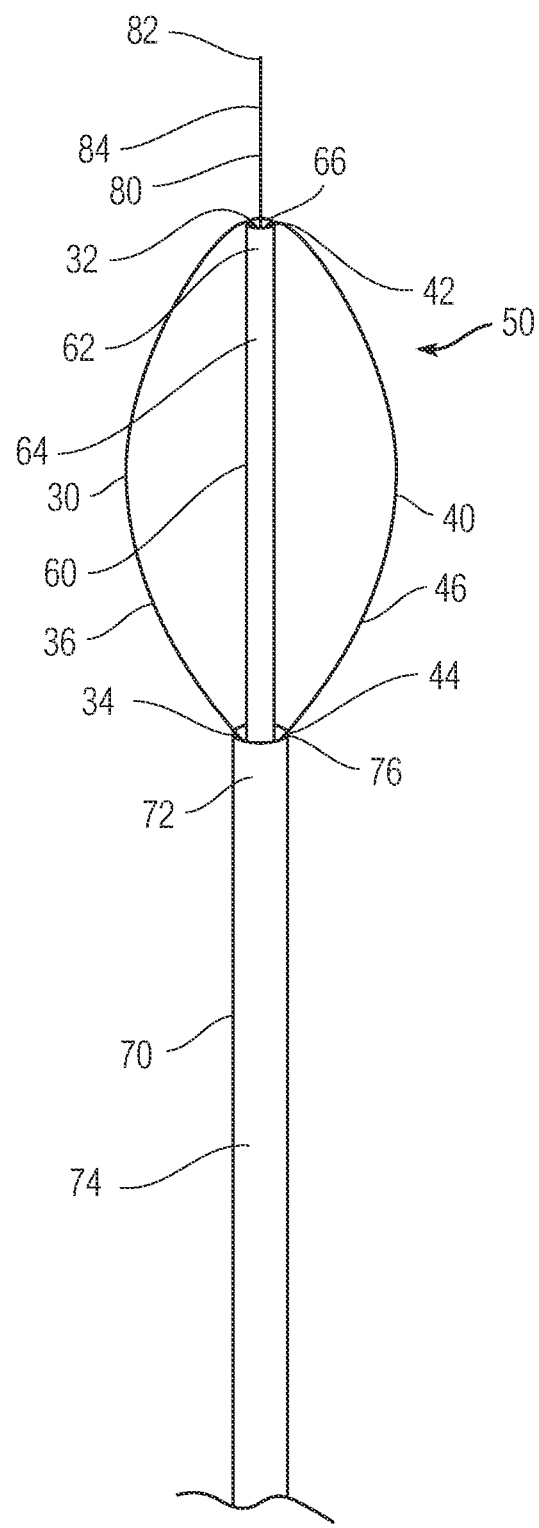

FIGS. 2a-b illustrate an embodiment of the mitral commissure locating system (50). According to one embodiment of the present teachings, the mitral commissure locating system (50) comprises a central catheter (60), a bow catheter (70), a guide wire (80), and two bow wires (30, 40). Each of the bow catheter (70) and the central catheter (60) has a proximal end (not shown), a distal end (62, 72), and an elongated tubular body (64, 74) comprising an axial lumen (66, 76) extending between the proximal and distal ends (62, 72), The guide wire (80) also comprises a proximal end (not shown), a distal end (82), and an elongated wire body (84) extending between the proximal (not shown) and distal ends (82). The proximal ends of the bow catheter (70), the central catheter (60) and the guide wire (80) are manipulated by a clinician from outside of the body. The distal ends (62, 72, 82) of the central catheter (60), the bow catheter (70), and the guide wire (80) are inserted into the heart percutaneously.

The guide wire (80) is slidably disposed within the axial lumen (66) of the central catheter (60). A clinician can extend the guide wire (80) distally so that the distal end (82) of the guide wire (80) is outside of the distal end (62) of the central catheter (60). A clinician can also retract the guide wire (80) proximally so that the distal end (82) of the guide wire (80) is within the axial lumen (66) of the central catheter (60).

The central catheter (60) is slidably disposed within the axial lumen (76) of the bow catheter (70). The bow wires (30, 40) also have proximal ends (34, 44), distal ends (32, 42), and elongated bow wires (36, 46) between the two ends. As illustrated in FIG. 2a, the distal ends (32, 42) of the bow wires (30, 40) are fixed to the central catheter (60) at or near its distal end (62), the proximal ends (34, 44) of the bow wires (30, 40) are fixed to the bow catheter (70) at or near its distal end (72). As the clinician extends the central catheter (60) distally, the distal end (62) of the central catheter (60) extends distally outside of the distal end (72) of the bow catheter (70). The length of bow wires (30, 40) limit the extent of the distal end (62) of the central catheter (60) beyond the distal end (72) of the bow catheter (70), as shown in FIG. 2a. As the clinician retracts the central catheter (60) proximally, the distal end (62) of the central catheter (60) moves proximally toward the distal end (72) of the bow catheter (70). As the proximal (34, 44) and distal ends (32, 42) of the bow wires (30, 40) draw closer, elongated bow wires (36, 46) extend radially outward as illustrated in FIG. 2b.

According to one embodiment of the present teachings, the mitral commissure locating system (50) comprises an elongated delivery profile and an expanded deployed profile. FIG. 2a illustrates an elongated delivery profile of the mitral commissure locating system (50). In this delivery profile, the central catheter (60) extends distally from within the axial lumen (76) of the bow catheter (70). The bow wires (30, 40) are in a generally straightened shape. The distal end (62) of the central catheter (60) and the distal end (72) of the bow catheter (70) are far apart from each other along the length of the bow wires (30, 40). The bow catheter (70), the bow wires (30, 40), and the central catheter (60) are packed tightly in their smallest radial profiles to be delivered through a delivery sheath (not shown).

FIG. 2b illustrates a deployed profile of the mitral commissure locating system (50). In this deployed profile, the central catheter (60) retracts proximally, drawing its distal end (62) closer to the distal end (72) of the bow catheter (70), the bow wires (30, 40) arc outward radially away from the longitudinal axis of the bow catheter (70). The portion of the central catheter (60) outside of the bow catheter (70) and the radically curved bow wires form a generally flat surface that is configured to fit at the slit between the posterior (10)

and anterior mitral leaflets (8). Alternatively, the radially curved bow wires (30, 40) form a gradually curved surface that fit within the curvature of the coaptation line from one commissure, across the mid anterior leaflet, to the other commissure so that valve leaflets are prevented from being held open during subsequent procedure.

In some embodiments of the present teachings, the bow wires (30, 40) are made of a material conventionally used fix guide wire (80). Examples of the material include a straight stainless steel wire, a coiled stainless steel wire, a glass fiber, a plastics material, nitinol, and etc. In one embodiment, the bow wires (30, 40) are made of an adaptable material that is configured to curve radically outward as its distal (32, 42) and proximal ends (34, 44) come together. In another embodiment, the bow wires (30, 40) are made of an adaptable material that at least a portion of the bow wires (30, 40) arc radially as the bow wires (30, 40) encounters tissues of a heart, for example, as described later in the present teachings.

According to one embodiment of the present teachings, the mitral commissure locating system (50) transitions from its delivery profile to its deployed profile by a clinician from outside of the body. That is, a clinician retracts the proximal end of the central catheter (60) proximally while holding the bow catheter (70) steady, reduces the distance between the distal ends of the central catheter (60) and bow catheter, and expands the bow wire radially. Alternatively, a clinician can push the proximal end of the bow catheter (70) distally while holding the central catheter (60) steady, thereby deploying the mitral commissure locating system (50). One skilled in the art should understand that mechanisms, steps, and details of the deployment can vary. What has been disclosed in the present teachings is only exemplary and should not be viewed as limiting.

Figure 3A:
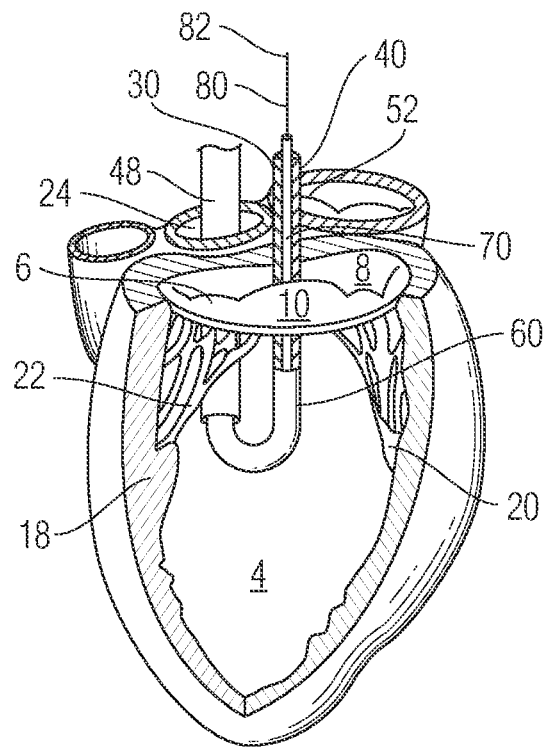
FIGS. 3a-3b are perspective views of an exemplary mitral commissure locating system percutaneously inserted across the mitral valve in accordance with certain embodiments of the present teachings.
Figure 3B:
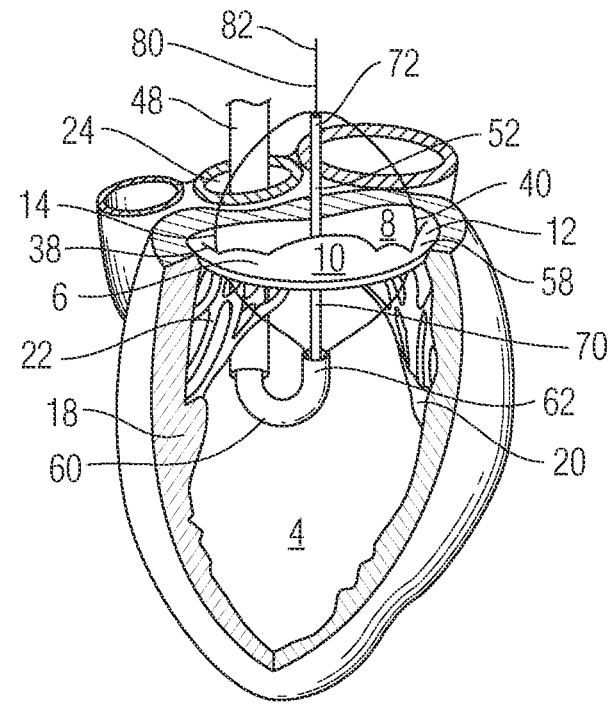

Now referring to FIGS. 3a-b, a mitral commissure locating system (50) is delivered and deployed at a mitral valve (6) according to one embodiment of the present teachings. What is described below are certain exemplary mitral commissure locating system (50) of the present teachings. One ordinarily skilled in the art would understand that other ways of percutaneous delivery can also be used without departing from the spirit of the present teachings. Thus the disclosure below should not be viewed limiting.

According to one embodiment of the present teachings, a delivery sheath (48) is directed into the aorta (24), through the aortic valve and into the left ventricle (4) between the tendinous chords (22). This delivery sheath (48) is then used as a conduit for the subsequent device delivery to the treatment site. Thus, the mitral commissure locating system (50) can be advanced through the delivery sheath (48) to the treatment location. One skilled in the art should understand, a delivery sheath (48) may not be necessary and the mitral commissure locating system (50) can be directly advanced to the treatment location.

FIG. 3a illustrates an exemplary mitral commissure locating system (50) being delivered across the mitral valve (6). According to certain embodiments of the present teachings, the mitral commissure locating system (50) in its delivery profile is delivered to the mitral valve (6). The mitral commissure locating system (50) comprises a distal portion (52). As illustrated in FIG. 3a, part of the distal portion (52) of the mitral commissure locating system (50), for example the portions of the system comprising the distal half of the bow wires (30, 40), is disposed inside of the left atrium (2) and the rest portion of the mitral commissure locating system (50) is disposed inside the left ventricle (4).

In one embodiment of the present teachings, the guide wire (80) is first inserted through the delivery sheath (48) and enters the left ventricle (4). A clinician can manipulate the guide wire (80) so that the distal end (82) of the guide wire (80) is steered to enter between the papillary muscles (18, 20), through the slit between the posterior (10) and anterior mitral leaflets (8), and into the left ventricle (4). In some embodiments, the distal end (82) of the guide wire (80) can be turned, rotated, or deflected. The delectability or steerability of the guide wire (80) allows a clinician to manipulate the distal end (82) of the guide wire (80) from outside of the body and advance to the mitral annular slit between the posterior (10) and anterior mitral leaflets (8), and further distally to the left pulmonary vein when needed. Design and construction of a steerable and deflectable guide wire (80) are known to those with ordinary skill in the art.

The central catheter (60), along with the bow catheter (70) and bow wires (30, 40), then tracks over the guide wire (80), so that the distal portion (52) of the mitral commissure locating system (50) is positioned across the mitral valve (6) as shown in FIG. 3a, Alternatively, the entire distal portion (52) of the mitral commissure locating system (50) including the guide wire (80), the central catheter (60), the bow wires (30, 40) and the bow catheter (70), is delivered together through the delivery sheath (48) and positioned across the mitral valve (6).

FIG. 3b illustrates the above described exemplary mitral commissure locating system (50) being deployed across the mitral valve (6). As the distal ends (62, 72) of the central catheter (60) and bow catheter (70) draw closer by a clinician from outside of the body, the bow wires (30, 40) curves outward. As the distal portion (52) of the mitral commissure locating system (50) is deployed, the generally flat plane formed by the bow wires (30, 40) automatically aligns along the slit between the posterior (10) and anterior mitral leaflets (8). As the bow wires (30, 40) further axes outward, each wire makes contact with a mitral valve commissure (12, 14). As the distal ends (62, 72) of the central catheter (60) and bow catheter (70) is drawn further closely by a clinician from outside of the body, the bow wires (30, 40) curves further outward, portions of the bow wires (30, 40) contact the mitral valve commissure (12, 14) and form narrow waists (38, 48) as they are obstructed from expanding further radially, as illustrated in FIG. 3b.

In an alternative embodiment, the distal portion of the mitral commissure locating system could be positioned inside a left pulmonary vein in order to stabilize the system for subsequent procedures. To achieve this, according to one embodiment of the present teachings, the bow wires are made long enough so that a proximal portion of the bow wires remain inside the left ventricle, a middle portion of the bow wires are inside the left atrium, and a distal portion of the bow wires are inside the left pulmonary vein. When deployed, as the bow wires curve radially outward, the radially expanded distal portion of the bow wire secures the distal position of the mitral commissure locating system inside the left pulmonary vein, and the radially expanded middle and proximal portions of the bow wires securely locked into the commissure as the heart contracts.

Figure 3C:
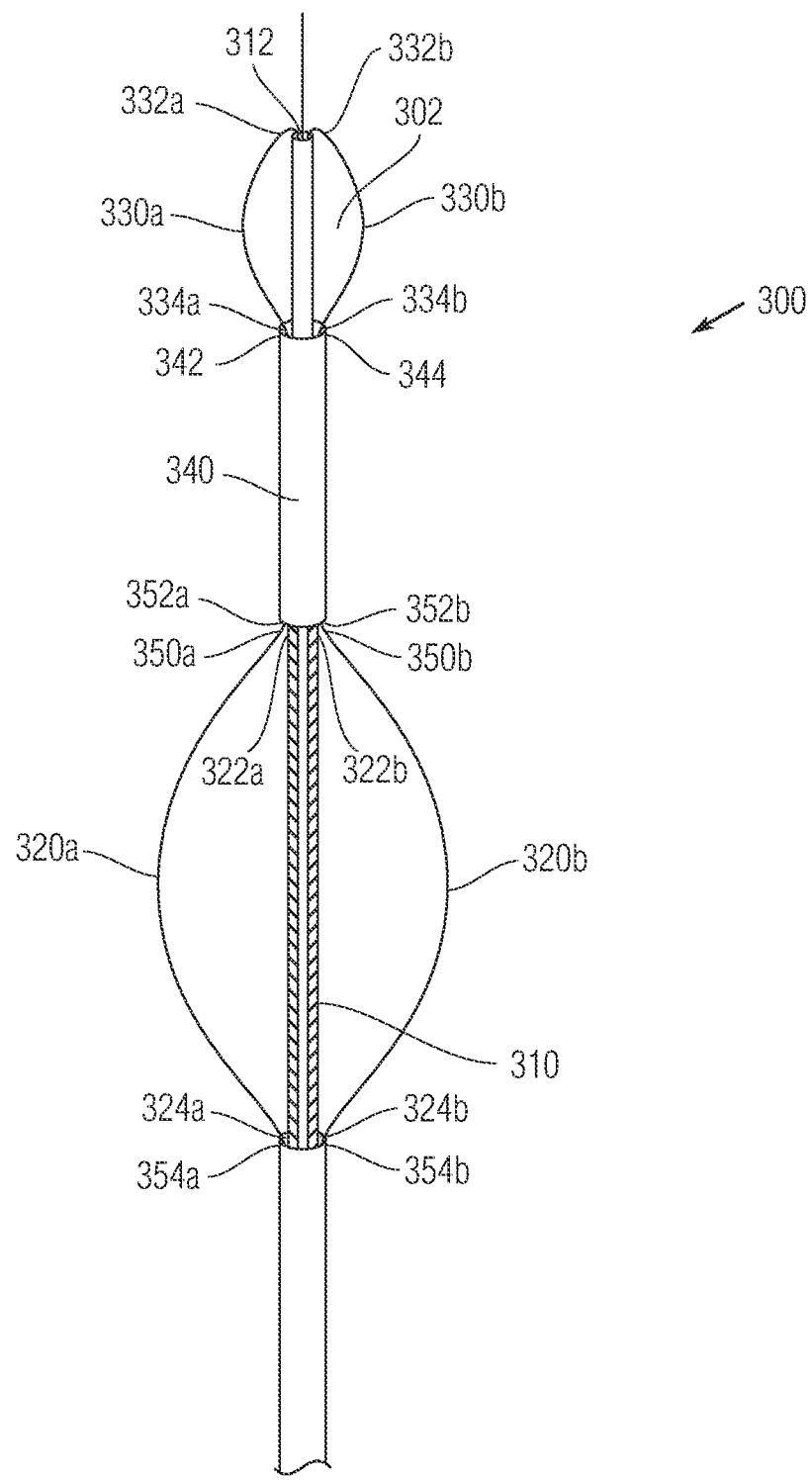
FIG. 3c is a perspective view of another exemplary mitral commissure locating system in accordance with the present teachings.
Figure 3D:
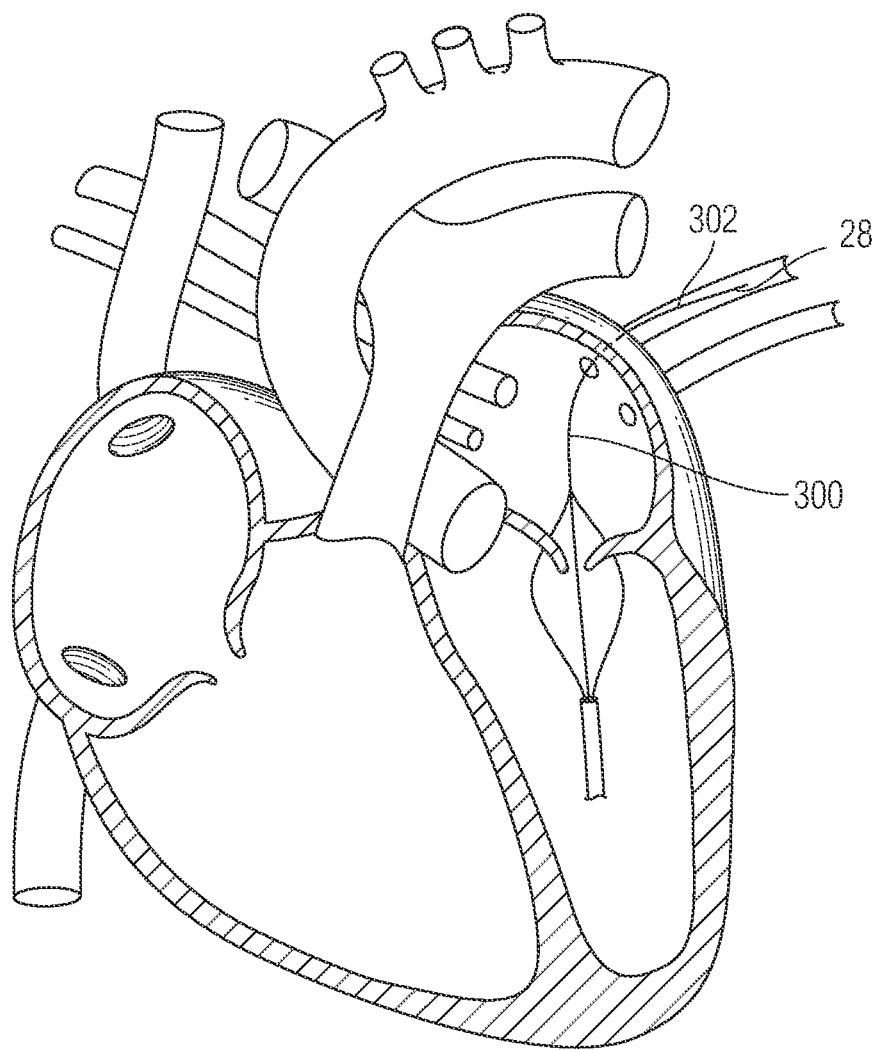
FIG. 3d is a perspective view of another exemplary mitral commissure locating system percutaneously inserted into the left heart in accordance with certain embodiments of the present teachings.

FIG. 3c illustrates another embodiment of the present teaching, where the distal portion (302) of the mitral commissure locating system (300) has a second bow catheter-bow wire system which allows the distal portion (302) of the mitral commissure locating system (300) to be deployed inside the left pulmonary vein (28), thereby by stabilizing the positioning of the mitral commissure locating system (300), One embodiment of such mitral commissure locating system (300) includes a central catheter (310) attached to a second pair of the bow wires (330a, 330b) at its distal end (312). The distal ends (332a, 332b) of the second pair of the bow wires (330a, 330b) attach to the distal end of the central catheter (310). The proximal ends (334a, 334b) of the second pair of the bow wires (330a, 330b) attach to the distal end (342) of the bow catheter (340). Similar to what has been described above, the central catheter (310) is slidably disposed within the longitudinal lumen (344) of the bow catheter (340). The bow catheter (340) further comprises a pair of side openings (350a, 350b) along its tubular wall. A first pair of bow wires (320a, 320b) have their proximal ends (324a, 324b) attaching to the proximal ends (354a, 354b) of the side openings (350a, 350b) on the bow catheter (340), and their distal ends (322a, 322b) attaching to the central catheter (310) along its tubular wall. The side openings (350a, 350b) are configured to allow the first pair of the bow wires (320a, 320b) to bend radially outward so that it can be locked inside the commissures (12, 14) when the distal end (312) of the bow catheter (340) and the distal end (342) of the central catheter (310) are drawn closer. The distance between the distal ends (322a, 322b) of the first pair of the bow wires (320a, 320b) and the proximal ends (334a, 334b) of the second pair of the bow wires (330a, 330b) are configured in such way that as the second pair of the bow wires (330a, 330b) are positioned inside the left pulmonary vein (28), the first pair of the bow wires (320a, 320b) are positioned across the mitral valve (6) between the mitral leaflets (8, 10). As the distal end (312) of the central catheter (310) is drawn closer to the distal end (342) of the bow catheter (340), the distal ends (322a, 322b, 332a, 332b) and proximal ends (324a, 324b, 334a, 334b) of both pairs of the bow wires (320a, 320b, 330a, 330b) are drawn closer at the same time. Both pairs of the bow wires (320a, 320b, 330a, 330b) curve radially outwardly. The first pair of bow wires (320a, 320b) are locked inside the commissures (12, 14) as the heart contracts, and the second pair of the bow wires (330a, 330b) secure the distal portion (302) of the mitral commissure locating system (300) inside the left pulmonary vein (28) as illustrated in FIG. 3d. One skilled in the art should understand that other mechanism which allows the distal portion of the mitral commissure locating system to be secured inside the left pulmonary vein can also be incorporated with the embodiment disclosed herein. For example, two central catheter-bow wire systems are constructed and put together, one to be deployed inside the left pulmonary vein, and the other to be deployed across the mitral valve. Thus, the specific embodiment provided in the present teachings should not be viewed as limiting. In one embodiment of the present teachings, the bow wires can include a radiopaque or echogenic marker so that the wire can be easily visualized by using radiographic imaging equipment such as with x-ray, magnetic resonance, ultrasound, or fluoroscopic techniques. The radiopaque marker can be in the form of threads, beads, or other forms. In some embodiments, radiopaque markers are attached to the wire. For example, the radiopaque markers can be wrapped, laminated, and/or bonded through a welding process. In another embodiment, the bow wire could be made of radiopaque material.

In one embodiment, by visualizing the narrow waist (38, 48) on the bow wires (30, 40), a clinician identifies the mitral valve commissure (12, 14). In another embodiment, by forming the narrow waist (38, 48) on the bow wires (30, 40), the deployed distal portion (52) of the mitral commissure locating system (50) is securely positioned across the mitral valve (6) for subsequent procedures.

In another embodiment, the bow wires of the mitral commissure locating system comprises a preformed reversed bends on the bow wires, which forms a narrow waist when deployed. In some embodiments, such reversed bends or the narrow waist fit into the mitral commissure and, as a result secure the mitral commissure locating system in the mitral annulus. Without being limited to any theory, such reversed bends/narrow waist of the mitral commissure locating system ensures a better positioning of the delivery catheter for the tissue piercing wire so that the distal end of the tissue piercing wire can be positioned close to the annulus.

Figure 4A:
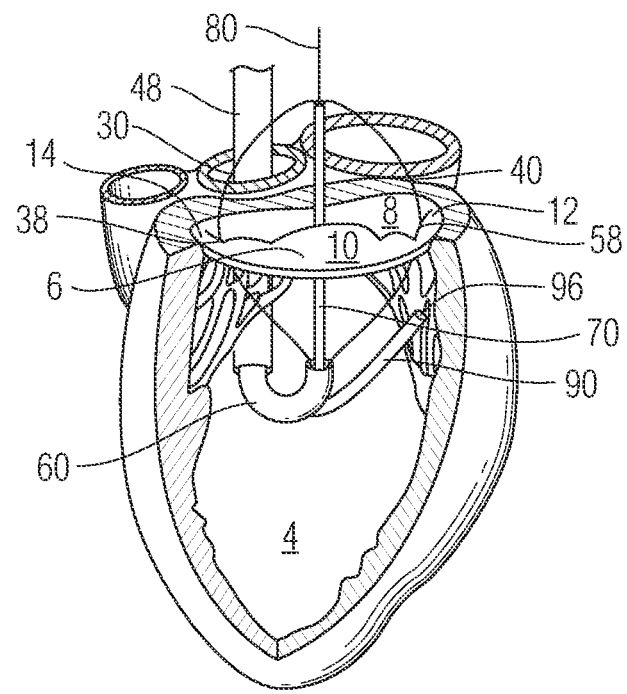
FIGS. 4a-4b are perspective views of an exemplary tissue piercing wire percutaneously deployed across the mitral annulus at a commissure in accordance with certain embodiments of the present teachings.

In one embodiment of the present teachings, upon marking the mitral valve commissure (12, 14) by the mitral commissure locating system (50), a clinician can then advance a delivery catheter for tissue piercing wire (device) (90) distally and position it adjacent, approximate to/or against the mitral annulus (16) at the mitral valve posteromedial commissure (12) from inside the left ventricle (4), as illustrated in FIG. 4a. In various embodiments of the present teachings, a tissue piercing wire (100) is pre-loaded within the lumen (96) of a delivery catheter for tissue piercing wire (90) during advancement of the delivery catheter of the tissue piercing wire (90) to the treatment site. In various other embodiments, the tissue piercing wire (100) is advanced through the lumen (96) after the delivery catheter of the tissue piercing wire (90) is placed at the treatment location.

Figure 4B:
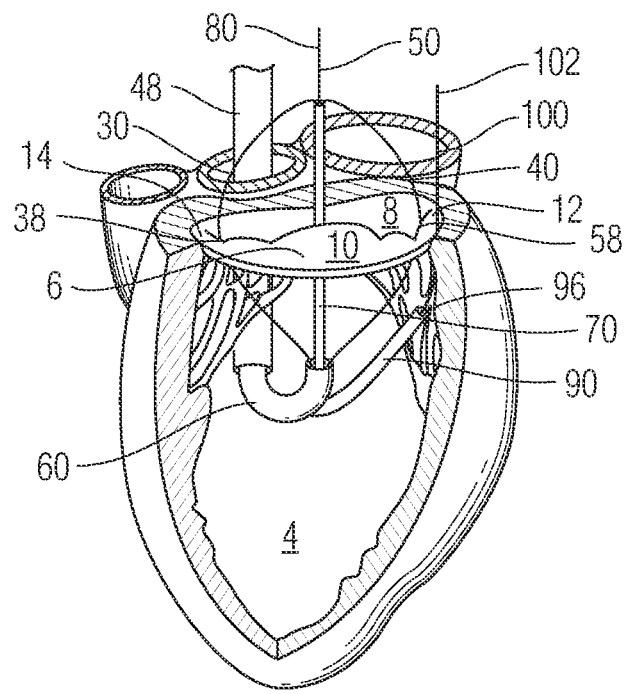

Once a delivery catheter is properly positioned, a tissue piercing wire (100) is advanced relative to the delivery catheter for tissue piercing wire (90) as illustrated in FIG. 4b. According to one embodiment, the distal end (102) of the tissue piercing wire (100) has a piercing tip which allows it to perforate the mitral annulus (16). In another embodiment, a radio frequency energy is then applied so that the distal piercing tip of the tissue piercing wire (100) is advanced through the mitral annuls (16) and reaches the left atrium (2). In yet another embodiment, the distal end of the delivery catheter is configured to pierce through the annulus. A wire then slides through the lumen of the delivery catheter to reach the opposite side of the annulus. One skilled in the art should understand that other structures that can serve the function of the tissue piercing wire are also included in the present teachings. Thus, the above discussion on tissue piercing wires should not be considered as limiting.

In some embodiments, the movement of a tissue piercing wire (100) is accomplished manually. Alternatively, the movement of a tissue piercing wire (100) may be automated and therefore requires additional controls such as a spring-loaded mechanism attached to the delivery.

Figure 5A:
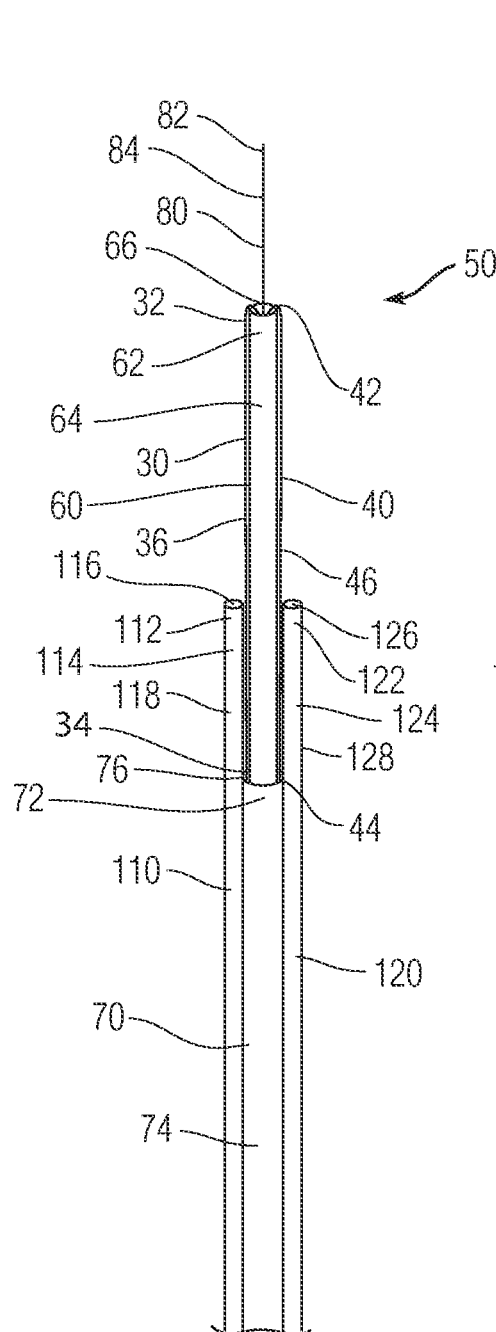
FIGS. 5a-5b are perspective views of an exemplary mitral commissure locating system in accordance the present teachings.
Figure 5B:
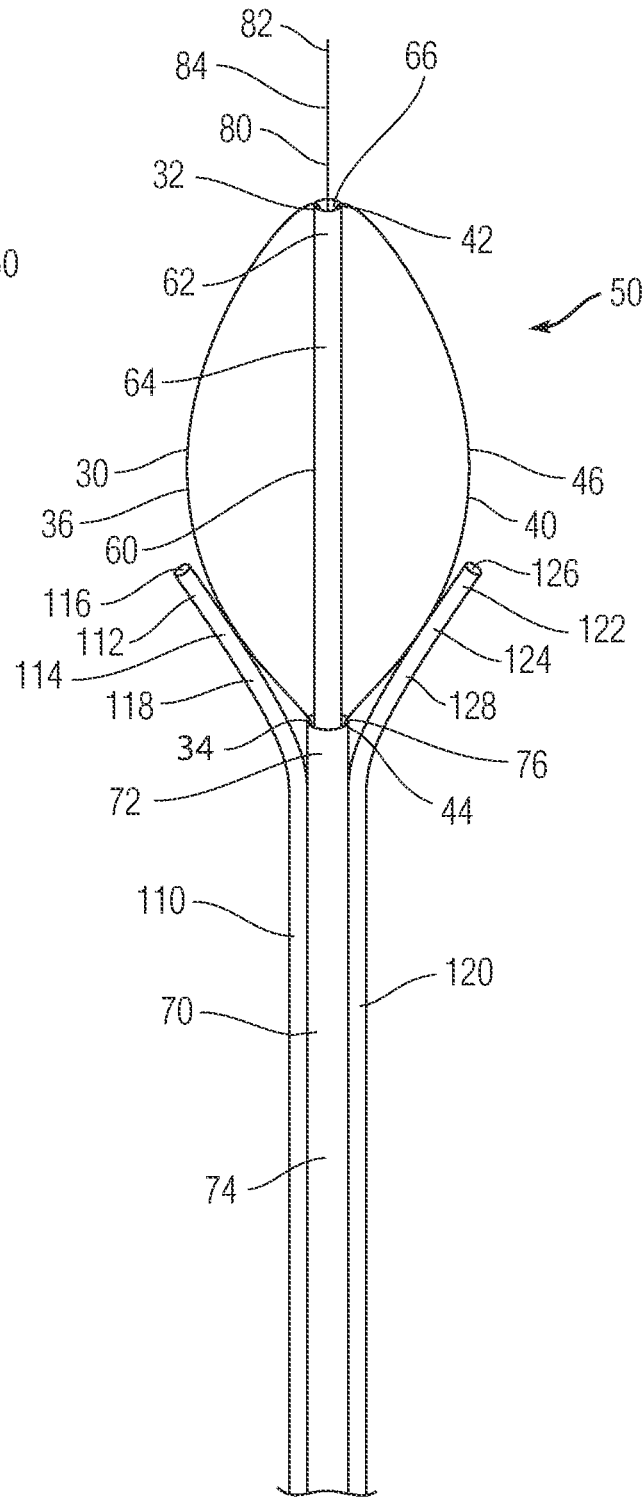

FIGS. 5a-5b illustrate another embodiment of the present teachings. In one embodiment, one delivery catheter for the tissue piercing wire (110, 120) attaches to each one of the bow wire (30, 40) of the mitral valve commissure system (50). Each delivery catheter for tissue piercing wire (110, 120) includes a proximal end (not shown) being manipulated by a clinician from outside of the body, a distal end (112, 122), and a tubular elongated body (114, 124) with an axial lumen (116, 126). According to some embodiments, the distal ends (112, 122) of the delivery catheter for tissue piercing wire (110, 120) are distal to the distal end (62) of the bow catheter (70) by a pre-defined distance. As illustrated in FIGS. 5a-5b, in one embodiment of the present teachings, a distal portion (118, 128) of each delivery catheter for tissue piercing wire (110, 120) attaches to a portion of the bow wire (30, 40) and the rest portion of the tissue piercing catheter (110, 120) connects to a portion of the bow catheter (70). These attachments allow the distal portion (118, 128) of each delivery catheter for tissue piercing wire (110, 120) to move along with the movement of each of the bow wires (30, 40). That is, as the distal ends (62, 72) of the central catheter (60) and the bow catheter (70) come together, the bow wires (30, 40) are radially outwardly and the distal portion (118, 128) of delivery catheter for tissue piercing wires (110, 120) are directed radially outwardly by the bow wires (30, 40) as illustrated in FIG. 5b.

In one embodiment, only portions of the delivery catheter for tissue piercing wire (110, 120) attaches to the bow catheter (70) and the bow wires (30, 40). In another embodiment, the entire length of the delivery catheter for tissue piercing wire (110, 120) either attaches to the bow wires (30, 40) or to the bow catheter (70). One skilled in the art should understand that the attachment between the delivery catheter for tissue piercing wire (110, 120) and the bow wires (30, 40) and the bow catheter (70) could vary according to the need of the design and function that needs to be achieved. For example, as the exemplary embodiment shown in FIG. 5b, a gap is present between the attachments of the delivery catheter for tissue piercing wire (110, 120) to the bow wires (30, 40) and to the bow catheter (70), which facilitates the radial bend of the distal portion (118, 128) of the delivery catheter for tissue piercing wire (110, 120) as show. In another exemplary embodiment, also shown in FIG. 5a, the very distal end portion of the delivery catheter for tissue piercing wire (110, 120) is not attached to the bow wires (30, 40), so that as the bow wires (30, 40) is deployed and marks the mitral valve commissure (12, 14), the distal end portion of the delivery catheter for tissue piercing wire (110, 120) directs further radially outward at a pre-defined angle and distance so that the distal ends (112, 122) of the delivery catheter for tissue piercing wire (110, 120) can be positioned precisely at the most desired treatment location.

According to one embodiment, the delivery catheter for tissue piercing wire (110, 120) attaches to the bow wires (30, 40) and the bow catheter (70) by a mechanical means including screws, bolts, clamps, bands, wire wraps, metal forms, or the like. According to another embodiment, the delivery catheter for tissue piercing wire (110, 120) attach to the bow wires (30, 40) and the bow catheter (70) by a chemical means, including an adhesive or the like. According to another embodiment, the delivery catheter for tissue piercing wire (110, 120) attach to the bow wires (30, 40) and the bow catheter (70) by chemical means, including ultrasonic welding, laser welding, overmolding, or the like. According to another embodiment, the delivery catheter for tissue piercing wire (110, 120) attach to the bow wires (30, 40) and the bow catheter (70) by other attachment means known to those skilled in the art. Yet in another embodiment, the delivery catheter for tissue piercing wire and the bow catheter are a single continuous tubular construction with an exit port cut on the tubular wall. In another embodiment, the tissue piercing wire is slidably disposed within the single lumen and exits the exit port on the tubular wall.

In one embodiment, the delivery catheter for tissue piercing wires (110, 120) are stationarily attached to the bow catheter (70) and bow wires (30, 40). That is, the delivery catheter for tissue piercing wires (110, 120) cannot move relative to the bow catheter (70) and bow wires (30, 40). In another embodiment, the delivery catheter fix tissue piercing wires (110, 120) are slidably attached to the bow catheter (70) and bow wires (30, 40). That is, the delivery catheter for tissue piercing wires (110, 120) could slide against the bow catheter (70) and bow wires (30, 40) while still remaining attached to the bow wires (30, 40) and bow catheter (70).

In one embodiment, one delivery catheter for tissue piercing wire attaches to each of the bow wires. In another embodiment, to achieve a small delivery profile, only one delivery catheter for tissue piercing wire attaches to only one of the bow wires. Thus, the specific disclosure herein should not be viewed as limiting.

Similar to what has been described above, this embodiment of the present teachings also has an elongated delivery profile and an expanded deployed profile. FIG. 5a illustrates an elongated delivery profile where the central catheter (60) extends distally from within the axial lumen (76) of the bow catheter (70). The bow wires (30, 40) are in a generally straightened shape. The distal end (62) of the central catheter (60) and the distal end (72) of the bow catheter (70) are far apart from each other to the length of the bow wires (30, 40). And the two delivery catheter for tissue piercing wires (110, 120) are packed closely to the central catheter (60) and to bow catheter (70) to form a small radial profile.

FIG. 5b further illustrates a deployment of the delivery catheter for tissue piercing wire (110, 120). In this deployed profile, the central catheter (60) retracts proximally, drawing its distal end (62) to the distal end (72) of the bow catheter (70) and the bow wires (30, 40) are outwardly radially away from the longitudinal axis of the bow catheter (70). The portion of the central catheter (60) outside of the bow catheter (70) and the radially curved bow wires form a generally flat surface. Following the radial movement of the bow wires (30, 40), the distal portions (118, 128) of the delivery catheter for tissue piercing wires (110, 120) are directed by the bow wires (30, 40) and pivot outwardly radially from the elongated axis of the central catheter (60) and the bow catheter (70).

Similar to described above, especially in relation to FIGS. 3a-3b, the mitral commissure locating system (50) along with the delivery catheter for tissue piercing wire (110, 120) are delivered and deployed across the mitral valve (6). Tracking along a guide wire (80) extending across the mitral valve, the mitral commissure locating system (50) is first delivered to the mitral valve (6), with its distal portion extending through the slit between the posterior (10) and anterior mitral leaflets (8). Then, as a clinician draws the distal ends (62, 72) of the central catheter (60) and the bow catheter (70) closer to each other, the bow wires (30, 40) curve outward. As the bow wires (30, 40) further arc outwardly, each wire makes contact with a mitral valve commissure (12, 14). As the distal ends (62, 72) of the central catheter (60) and the bow catheter (70) draw further closely by a clinician from outside of the body, the bow wires (30, 40) curve further outwardly until the portion of the bow wires (30, 40) contacting the mitral valve commissure (12, 14) are obstructed from expanding further radially and forming a narrow waist (38, 48) similar to what has been shown in FIG. 3b.

In one embodiment where the distal portions (118, 128) of the delivery catheter for tissue piercing wire (110, 120) stationarily attaches to the bow wires (30, 40), the deployment of the bow wire (30, 40) directs the distal portion (118, 128) of the delivery catheter for tissue piercing wire (110, 120) radially outwardly. The distal ends (112, 122) of the delivery catheter for tissue piercing wire (110, 120) are positioned adjacent, approximate to, or against the mitral annulus (16) and inside the left ventricle (4) at or near the mitral valve commissure (12, 14). Alternatively, where the distal portion (118, 128) of the delivery catheter for tissue piercing wire (110, 120) slidably attaches to the bow wires (30, 40), after the bow wires (30, 40) mark the mitral valve commissure (12, 14), the delivery catheter for tissue piercing wires (110, 120) slides distally along the bow wires (30, 40) and the bow catheter (70) so that distal ends (112, 122) are positioned adjacent, approximate to, or against the mitral annulus (16) and inside the left ventricle (4) at or near the mitral valve commissure (12, 14).

In another embodiment, as the bow wires (30, 40) are deployed, the distal ends (112, 122) of the delivery catheter for tissue piercing wires (110, 120) are positioned inside the left atrium (2). In such an event, the clinician can retract the entire mitral commissure locating system (50) along with the delivery catheter for tissue piercing wires (110, 120) proximally, so that the distal ends (112, 122) of the delivery catheter for tissue piercing wires (110, 120) are retracted back into the left ventricle (4) and positioned adjacent, approximate to, or against the mitral annulus (16). Alternatively, instead of retracting the entire mitral commissure locating system (50) and the delivery catheter for tissue piercing wires (110, 120), the delivery catheter for tissue piercing wires (110, 120) slide proximally along the bow wires (30, 40) and bow catheter (70) so that the distal ends (112, 122) are positioned approximately to the mitral annulus (16).

In another embodiment; as the bow wires (30, 40) are deployed, the distal ends (112, 122) of the delivery catheter for tissue piercing wires (110, 120) are at a position that is inside the left ventricle (4) and distant to the mitral annulus (6). In such an event, the clinician can advance the entire mitral commissure locating system (50) along with the delivery catheter for tissue piercing wires (110, 120) proximally, so that the distal ends (112, 122) of the delivery catheter for tissue piercing wires (110, 120) are advanced distally and positioned adjacent, approximate to, or against the mitral annulus (16). Alternatively, instead of advancing the entire mitral commissure locating system (50) and the delivery catheter for tissue piercing wires (110, 120), the delivery catheter for tissue piercing wires (110, 120) slide distally along the bow wires (30, 40) and the bow catheter (60) so that distal ends (112, 122) are positioned approximate to the mitral annulus (16).

In yet another embodiment, the distal ends (112, 122) of the delivery catheter for tissue piercing wires (110, 120) include one or more radiopaque markers so that they can be easily visualized by using a radiographic imaging equipment such as with x-ray, magnetic resonance, ultrasound, or fluoroscopic techniques. With the visual assistance provided by the radiopaque marker, during the deployment of the mitral commissure locating system (50), a clinician can adjust the positioning of the system (50) and the delivery catheter for tissue piercing wire (110, 120) jointly or separately, so that the distal ends (112, 122) of the delivery catheter for tissue piercing wires (110, 120) remain approximate to the mitral annulus (16).

Once the delivery catheter for tissue piercing wires are properly positioned, the tissue piercing wires are then advanced relatively to the delivery catheter for tissue piercing wire similar to what has been described above, including in FIG. 4b. Similarly, according to one embodiment, the distal ends of the tissue piercing wires have piercing tips which allow them to perforate the annulus. In another embodiment, one or both of the distal ends of tissue piercing wires has a radio frequency (RF) energy delivery tip to assist its crossing of the annulus. In one embodiment, the two tissue piercing wires are advanced simultaneously across the annulus. In another embodiment, the two tissue piercing wires are advanced sequentially across the annulus.

According to some embodiments, the tissue piercing wires advance inside the wire delivery lumen (116, 126) of the delivery catheter for tissue piercing wire (110, 120) and cross the annulus. According to some embodiments, the tissue piercing wires are preload inside the wire deli very lumen (116, 126) and the delivery catheter for tissue piercing wires (110, 120) having the tissue piercing wires disposed inside are then positioned at a treatment location. In some embodiments, after the delivery catheter for tissue piercing wires (110, 120) are positioned at the treatment location, the multiple tissue piercing wires then advance distally and cross the annulus. In certain embodiments, the multiple tissue piercing wires advance simultaneously. In certain embodiments, the multiple tissue piercing wires advance sequentially. In certain embodiments, the multiple tissue piercing wires advance in groups.

According to some embodiments, the distal portion of the tissue piercing wire is configured to deflect or curl back to prevent inadvertent tissue damage. The ability to deflect or curl can be achieved by the geometrical construct of the tissue piercing wire, such as a flexible distal portion, by the physical property of the material used in making the wire, or by the shape memory property of the material used in making the tissue piercing wire. Those skilled in the art would be able to incorporate known techniques and/or materials to achieve this purpose without undue experimentation.

Figure 6:
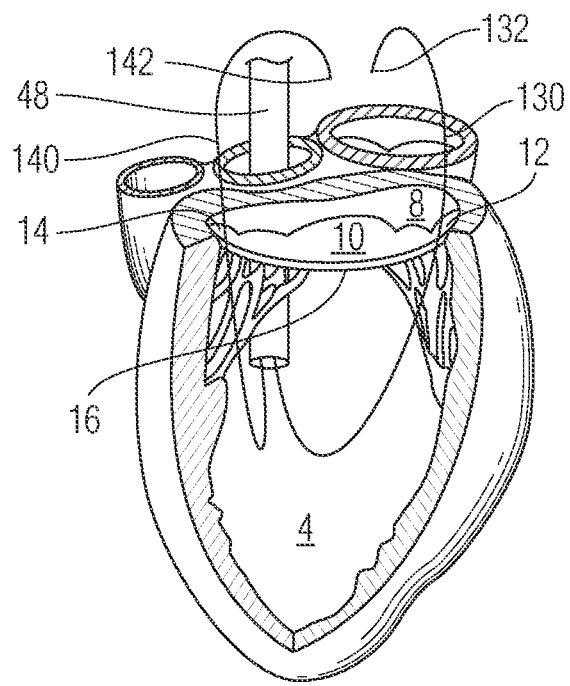
FIG. 6 is a perspective view of two exemplary tissue piercing wire percutaneously deployed across the mitral annulus at both the commissure in accordance with certain embodiments of the present teachings.

With the tissue piercing wire crossed the mitral annulus (16) at the mitral valve commissure, the mitral commissure locating system (50) along with the delivery catheter for tissue piercing wire are then removed from the body, leaving the tissue piercing wire remain across the mitral annulus (16) and mark the mitral valve commissure. FIG. 6 illustrates two tissue piercing wires (130, 140) remaining across the mitral annulus (16) at the mitral valve commissures (12, 14), with the distal ends (132, 142) of the tissue piercing wires (130, 140) inside the left atrium and the proximal ends (not shown) of the tissue piercing wires (130, 140) extending percutaneously outside of the body. In one embodiment, the two tissue piercing wires (130, 140) are simultaneously or sequentially positioned through two delivery catheter for tissue piercing wires attached to a mitral valve commissure locating system (50), for example as explained in detail above. In one embodiment, the two tissue piercing wires (130, 140) are sequentially positioned through one delivery catheter for tissue piercing wire attached to a mitral valve commissure locating system (50). For example, upon deploying one tissue piercing wire across the mitral annulus (16) at the posteromedial commissure (12), as explained in greater detail above, a clinician transitions the mitral valve commissure locating system (50) from its expanded deployed profile back to its elongated delivery profile, and removes it proximally to detach from the first tissue piercing wire positioned across the mitral annulus. The clinician then torques the mitral valve commissure locating system (50) along with the delivery catheter fix tissue piercing wire, so that the distal end of the delivery catheter for tissue piercing wire is positioned near the anterolateral commissures (14). A second tissue piercing wire is then deployed across the mitral annulus (16) at the anterolateral commissures (14). According to one embodiment of the present teachings, the tissue piercing wires are placed at the commissures (14, 16).

According to one embodiment of the present teachings, two tissue piercing wires are positioned across the mitral annulus. One skilled in the art should understand that any number of tissue piercing wires can be placed with the assistant of the mitral commissure locating system.

Although the present teachings provide tissue piercing wires that are placed across the commissures, one skilled in the art should understand that tissue piercing wire can be placed not only at the commissure, but also at other locations along the annulus, for example, the P1, P2, or P3 area of the posterior annulus. For example, the path of the tissue piercing wire can be adjusted by either steering its delivery catheter or by adjusting the degree of bend of the bow wire. And subsequently, tissue anchors can be placed at the locations marked by the tissue piercing wire, and the annulus between the tissue anchors are then plicated as described below.

According to one embodiment, the bow wires transitions together from its generally straightened profile to its bend profile. In another embodiment, two bow wires can be adjusted independently of each other so that one wire can have a different degree of bend from the other wire.

According to one embodiment, the delivery catheter fix the tissue piercing wire attaches to the bow wires at its distal end. In another embodiment, the delivery catheter for the tissue piercing wire attaches to the bow catheter at the distal end of the bow catheter. In yet another embodiment, the delivery catheter for the tissue piercing wire can attach to either of the bow wires or the bow catheter at any location needed. Thus, the specific embodiments disclosed here should not be viewed as limiting.

Figure 7:
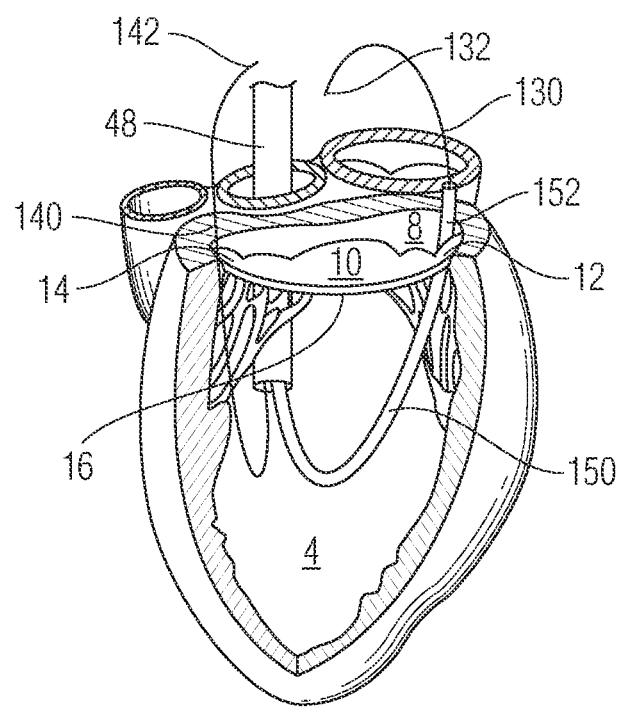
FIG. 7 is a perspective view of an exemplary tissue anchor delivery catheter percutaneously tracking over an exemplary tissue piercing wire across mitral annulus at a commissure in accordance with certain embodiments of the present teachings.

According to one embodiment, a first tissue anchor (160) can then be deployed over the tissue piercing wires (130, 140) and across the mitral annulus (16) at the mitral valve commissures (12, 14). According to some embodiments, as illustrated in FIG. 7, a first tissue anchor delivery catheter (150) tracks along the tissue piercing wire (130), across the mitral annulus (16), and into the left atrium (2). In certain embodiments, the first tissue anchor delivery catheter (150) is used to deliver a first tissue anchor (60) to the mitral annulus (16).

Figure 8:
FIG. 8 is a perspective view of an exemplary tissue anchor in accordance with the present teachings.

While any first tissue anchoring devices known in the art can be used, the particular tissue anchor in the present teachings, as shown in FIG. 8, is collapsible. In various embodiments, the particular tissue anchor in the present teachings comprises a plurality of discrete, fiat, or flexible anchor elements coupled with a flexible tensile member. The anchor elements can be made from a surgical grade fabric material (e.g., a polyester material such as DACRON). In some instances, designed to promote tissue in-growth so that the anchors become at least in part encased in tissue overtime. The anchor elements are coupled to a tensile member, in this example, a suture, by threading the suture distally through the anchor elements and proximally through the anchor elements. A slip knot or another type of locking mechanism is formed so that when a proximal end portion of the tensile member is pulled, all of the anchor elements will be drawn together. This leaves a long "tail" of the suture leading from the anchor to the venous access site and the long "tail" can be used for the subsequent tensioning and plication, as described herein.

Examples of tissue anchors and tissue anchor delivery catheters described in conjunction with the drawings of the present teachings have some similarities to those in U.S. patent application Ser. No. 12/273,670, filed on Nov. 19, 2008, entitled Tissue Anchor and Anchoring System, U.S. patent application Ser. No. 11/174,951, filed on Jul. 5, 2005, entitled First Tissue Anchor and Anchoring System and Methods of Using the Same, U.S. patent application Ser. No. 13/777,042, filed on Feb. 26, 2013, entitled Tissue Anchor and Anchoring System, each of which is incorporated by reference herein in its entirety. Although not shown in the exemplary figures, other suitable tissue anchoring devices can also be used. Examples of suitable tissue anchoring devices include, but are not limited to, tissue fasteners, tissue pledgets, or tissue staples etc.

Figure 9A:
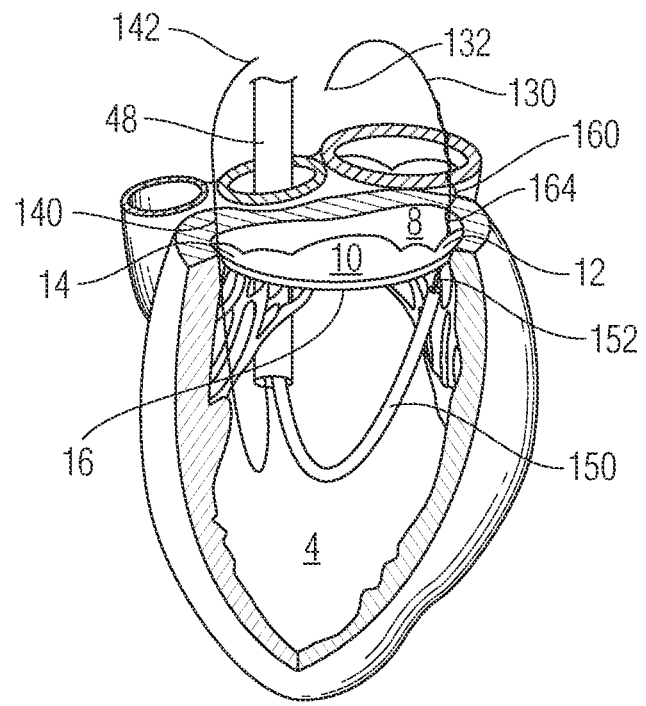
FIGS. 9a-9c are perspective views of an exemplary tissue anchor percutaneously deployed across the mitral annulus at a commissure in accordance with certain embodiments of the present teachings.
Figure 9B:
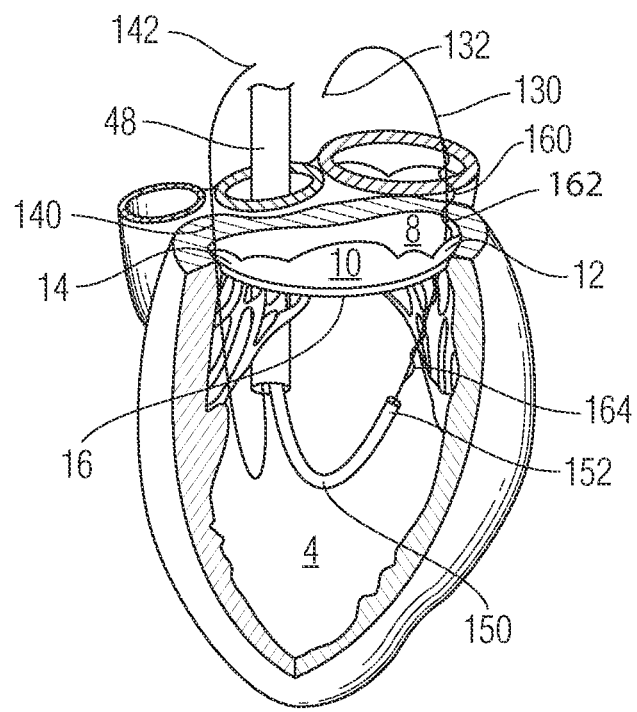

Still referring to FIG. 7, a first tissue anchor delivery catheter (150) holding a first tissue anchor (160) inside its longitudinal lumen (152) tracks along the wire (130), across the mitral annulus (16), and with the distal end (152) of the first tissue anchor delivery catheter (150) inside the left atrium (2). FIG. 9a illustrates that the first tissue anchor (160) is partially pushed distally outside of the distal end (152) of the first tissue anchor delivery catheter (150). Once the distal portion (162) of the first tissue anchor (160) or a sufficient amount of the anchor elements is exposed inside the left atrium (2) a clinician stops pushing the first tissue anchor (160) distally and retracts the first tissue anchor delivery catheter (150) proximally so that the distal end (152) of the first tissue anchor delivery catheter (150) moves proximally across the annulus (16) and back into the left ventricle (4), The clinician then exposes the proximal portion (164) of the first tissue anchor (160) or the remainder of the anchor elements of the first tissue anchor (160) within the left ventricle (4) by further retracting the first tissue anchor delivery catheter (150) proximally as shown in FIG. 9b.

Figure 9C:
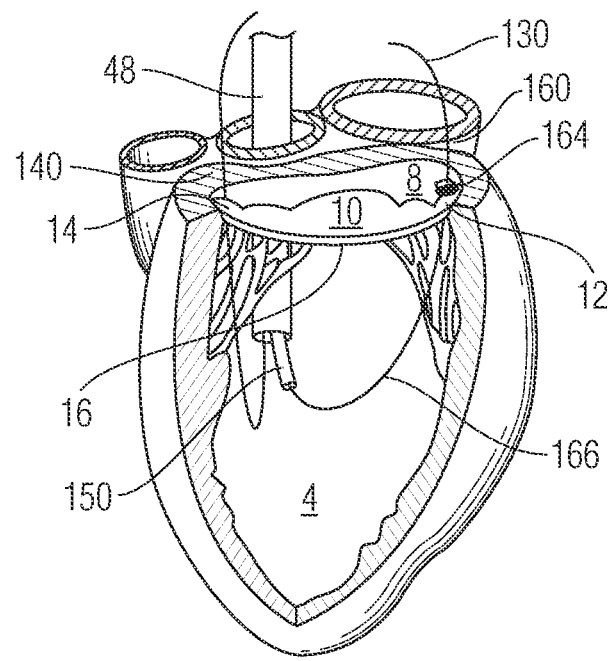

FIG. 9c illustrates the deployment of the first tissue anchor (160). A clinician pulls the proximal end of the tensile member (166) of the first tissue anchor (160) such that the anchor elements of the first tissue anchor (160) are drawn together against the opposite sides of the mitral annulus (16), thereby securing the first tissue anchor (160) to the mitral annulus (16) at the first mitral valve commissure. As a result, as illustrated in FIG. 9c, the first tissue anchor (160) is deployed across the mitral annulus (16) at the posteromedial commissure (12) with the distal portion of the first tissue anchor (160) placed against the atrial side of the mitral annulus (16), the proximal portion of the first tissue anchor (160) placed against the ventricle side of the mitral annulus (16), and the tensile member (166) of the first tissue anchor (160) extending proximally through the lumen (156) of the first tissue anchor delivery catheter (150) to the outside of the body. One skilled in the art should understand that although FIG. 9c shows a first tissue anchor is deployed across the mitral annulus at the posteromedial commissure (12) the first tissue anchor can also be deployed across the mitral annulus at the anterolateral commissures (14). Thus, what has been disclosed here should not be viewed as limiting.

In an alternative embodiment, after the first tissue anchor (160) is deployed across the mitral annulus, a clinician cinches/deploys the distal part of the tissue anchor on the atrial side of the annulus before retracts the anchor delivery catheter and deploys the proximal part of the anchor in the left ventricle. In a particular embodiment, a clinician exposes the distal portion of the tissue anchor inside the left atrium and cinches the anchor elements of the distal portion of the tissue anchor so that they are placed against the left atrial side of the annulus. In another embodiment, a clinician exposes and cinches the proximal portion of the tissue anchor from inside the left ventricle.

Figure 10:
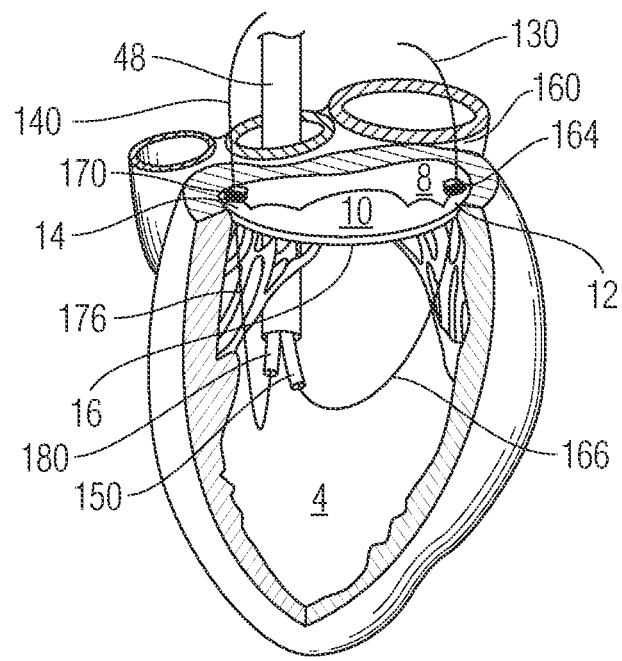
FIG. 10 is a perspective view of two exemplary tissue anchors percutaneously deployed across the mitral annulus at both commissures in accordance with certain embodiments of the present teachings.

With the first tissue anchor (160) securely deployed at the first mitral valve commissure across the mitral annulus (16), the clinician can deploy a second tissue anchor (170) at a second mitral valve commissure according to some embodiments of the present teachings. FIG. 10 illustrates an exemplary deployment of a second tissue anchor (170) across the mitral annulus (16) at a second mitral valve commissure. According to some embodiments, similar to what is described in FIGS. 9a-9c, a clinician uses similar steps to deploy a second tissue anchor (170) through the second tissue piercing wire (140) positioned at the second mitral valve commissure. As illustrated in FIG. 10, the second tissue anchor (170) is deployed across the mitral annulus (16) at the anterolateral commissure (14) with the distal portion of the second tissue anchor (170) placed against the atrial side of the mitral annulus (16), the proximal portion of the second tissue anchor (170) placed against the ventricle side of the mitral annulus (16), and the tensile member (176) of the second tissue anchor (170) extending proximally through the lumen (186) of the second tissue anchor delivery catheter (180) to the outside of the body.

According to some embodiments, a clinician can then apply tension to one or both of the tensile members (166, 176) of the first and second tissue anchors (160, 170). This tension pulls two tissue anchors (160, 170) closer to each other, thereby reducing the circumference of the mitral annulus. This tension, and the reduced distance between the two tissue anchors (160, 170), are maintained by directing a locker (184) along the tensile member (166, 176) towards the two tissue anchors (160, 170). The two wires (130, 140) and/or the two tissues anchor delivery catheters (150, 180) can then be retracted proximally and removed.

Suitable lockers include those known in the art and those described in U.S. application Ser. No. 11/753,921 filed on May 25, 2007, entitled Lockers for Surgical Tensile Members and Methods of Using the Same to Secure Surgical Tensile Members, the disclosure of which is incorporated herein by reference. With the tensile members secured by the locker, the excess tensile members proximal to the locker can be removed by a cutter, for example, a cutter disclosed in U.S. patent application Ser. No. 11/935,054, filed on Nov. 5, 2007, entitled Suture Cutter and Method of Cutting Suture, the disclosure of which is incorporated herein by reference.

FIGS. 11a-11d illustrate another embodiment of the mitral annulus (16) plication. As illustrates in FIG. 11a, according to one embodiment of the present teachings, upon the first tissue piercing wire (130) positioned across the mitral annulus (16) at the first mitral valve commissure, a bident catheter is introduced into the left ventricle (4) with one lumen of the bident catheter sliding over the first tissue piercing wire (130). Examples of the bident lumen catheter are disclosed in U.S. patent application Ser. No. 13/282,139, filed on Oct. 26, 2011, entitled Hand Operated Device for Controlled Deployment of a First tissue anchor (160) and Method of Using the Same, the disclosure of which is incorporated herein by reference.

A bident catheter, for example is a double lumen catheter with the distal portions of the two catheter members separating from each other and the rest portion of the two catheter members joined together. The distal portions of the two catheter members are kept close to each other during a percutaneous delivery. Once reaching the treatment location, the distal portion of the two catheter members are deployed to be radially apart from each other, either automatically by the construct of the bident catheter; or manually by a control mechanism from outside of the body. Each catheter lumen is used to deliver one tissue anchor, similar to what has been described above.

Alternatively, a tissue anchor delivery catheter with a single lumen catheter and a translation mechanism allowing catheter to be controllably moved to a second location can be used instead of a bident catheter. Examples of the delivery catheter with a translation mechanism is disclosed in U.S. Patent Application Ser. No. 61/786,373, filed on Mar. 15, 2013, entitled Translation Catheters, Systems, and Method of Use Thereof the disclosure of which is incorporated herein by reference.

Figure 11A:
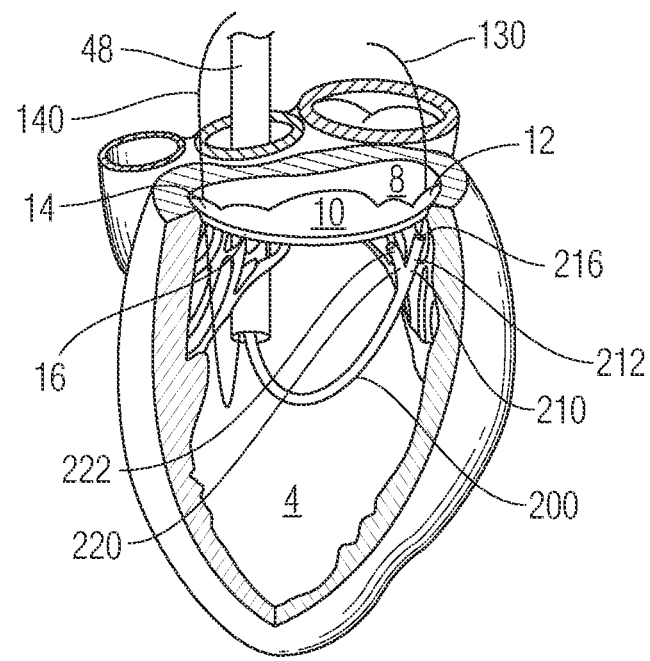
FIGS. 11a-11d are perspective views of multiple exemplary tissue anchors percutaneously deployed across the mitral annulus in accordance with certain embodiments of the present teachings.
Figure 11B:
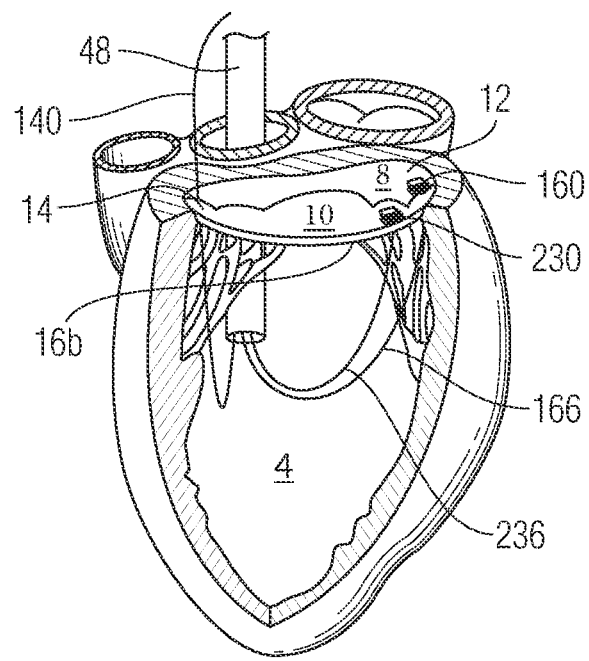

In one embodiment of the present teachings, a bident tissue anchor delivery catheter (200) comprises a first catheter member (210) having a lumen (216) threaded over the first tissue piercing wire (130) at the first mitral valve commissure. Once the distal end (212) of the first catheter member (210) is positioned approximately to the mitral annulus (16) at the first mitral valve commissure, the distal portion of the second catheter member (220) is deployed radially and laterally away from the distal portion of the first catheter member (210). In one embodiment, the distal end (222) of the second catheter member (220) directs generally to the mitral annulus (16) at the P3 region generally along the posterior mitral annulus (16b), as illustrated in FIG. 11a. A third tissue piercing wire is then delivered, followed by a third tissue anchor (230) deployed across the mitral annulus (16) at the P3 region. As shown in FIG. 11b, two tissue anchors (160, 230) are deployed across the mitral annulus (16), one at the posteromedial commissure (12) and the other at the P3 region of the posterior annuls (16b). The distal portions of the two tissue anchors (160, 230) are placed against the atrial side of the mitral annulus (16), the proximal portions of the two tissue anchors (160, 230) are placed against the ventricle side of the mitral annulus (16), and the tensile member (166, 236) of the two tissue anchors (160, 230) extend proximally to the outside of the body.

Similar to what has been described above, according to some embodiments, a clinician can then apply tension to one or both of the tensile members (166, 236) of the two tissue anchors (160, 230). This tension pulls two tissue anchors (160, 230) closer to each other, thereby plicating the annulus between the two tissue anchors (160, 230). This tension and the reduced distance between the two tissue anchors (160, 230) are maintained by directing a locker (238) along the tensile members (166, 236) towards the two tissue anchors (160, 230), as illustrated in FIG. 11c.

Figure 11C:
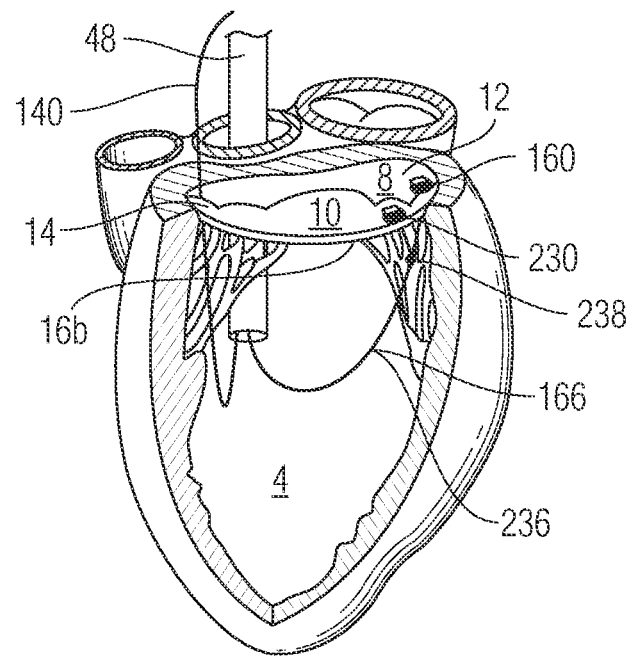
Figure 11D:
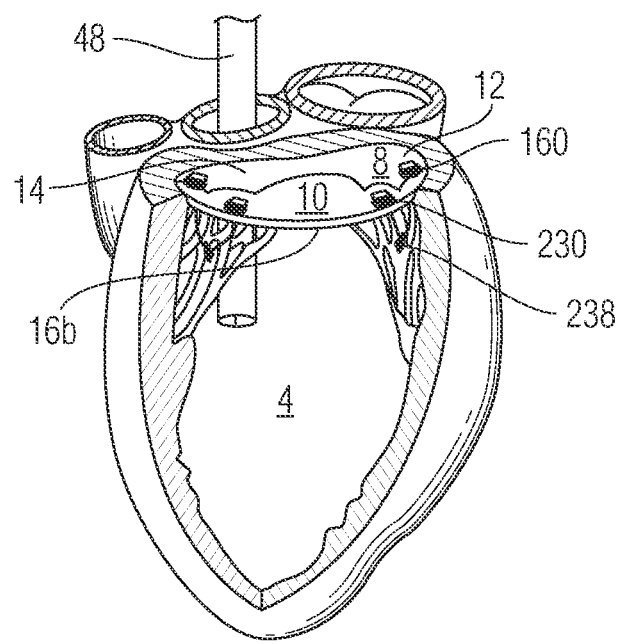

According to some embodiments, similar to what is described in FIGS. 11a-11c, a clinician uses similar steps to introduce another bident catheter (or a catheter with a translation mechanism) into the left ventricle (4) with one catheter lumen of the bident catheter sliding over the second tissue piercing wire (140), and the distal end of the first catheter member positioned approximately to the mitral annulus (16) at the second mitral valve commissure and the distal end of the second catheter member directed generally to the mitral annulus (16) at the P1 region generally along the posterior mitral annulus. Two tissue anchors are then deployed across the mitral annulus (16) with one at the second mitral valve commissure and the other at the P1 region generally along the posterior mitral annulus. FIG. 11d illustrates a third and a fourth tissue anchors deployed across the mitral annulus with one at the anterolateral commissures (14) and the other one at the P1 region generally along the posterior mitral annulus. A clinician applies tension to one or both of the tensile members of the third and fourth tissue anchors and locks the tension with a locker, thereby plicating the mitral annulus (16) between the two anchors, as shown in FIG. 11d.

Figure 12A:
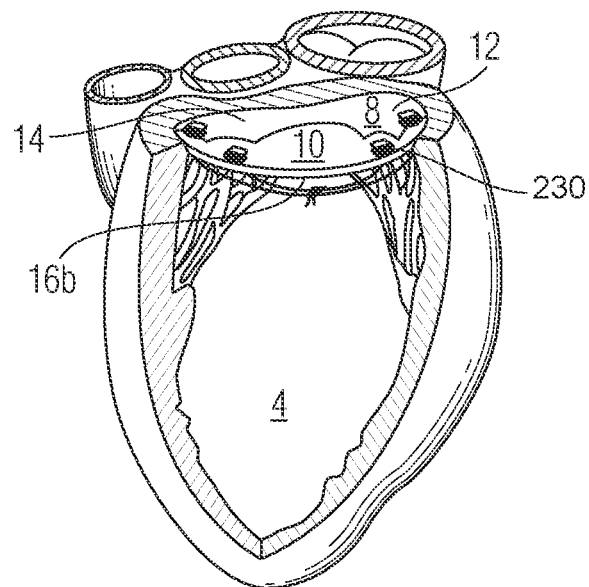
FIGS. 12a-12b are perspective views of tissue plication with multiple exemplary tissue anchors across the mitral annulus in accordance with certain embodiments of the present teachings.
Figure 12B:
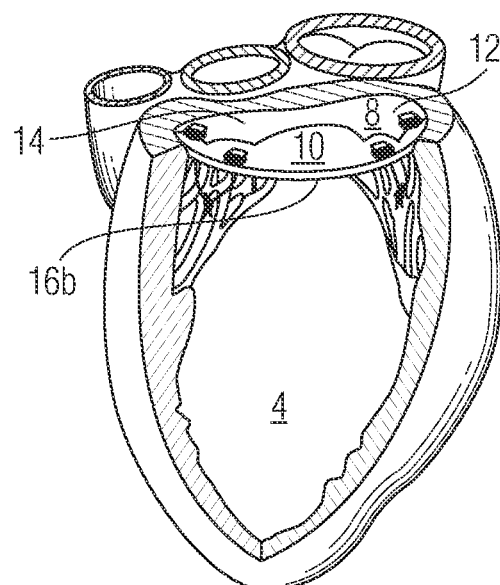

FIGS. 12a-12b illustrate four tissue anchors deployed across the mitral annulus (16) along the posterior annulus according to one embodiment of the present teachings. The first tissue anchor is deployed at the posteromedial commissure (12), the second one is deployed at the P3 region generally along the posterior mitral annulus, the third one is deployed at the anterolateral commissure (14), and the fourth one is deployed at the P1 region generally along the posterior mitral annulus. In one embodiment, a clinician applies tension to at least one of the four tissue anchors and locks such tension with one locker, as illustrated in FIG. 12*a*. In another embodiment, a clinician locks the tension between the adjacent tissue anchors with one locker as illustrated in FIG. 12*b*.

Without limiting the present teachings to any particular theory, the commissure areas have generally better structures than other areas since they are closer to the fibrous skeleton of the heart and, therefore may provide a stronger base to pull the dilated posterior annulus in the antero-posterior direction. Mitral annulus plication with one tissue anchor placed at a commissure provides a significant dimensional change in the antero-posterior direction which, without limiting the present teachings to any particular theory, is generally thought to be important for correcting a mitral regurgitation caused by a dilated annulus. In various embodiments of the present teachings the mitral commissure locating system uses the anatomical geometry of a heart for precisely placing tissue anchors described in the present application. Using the mitral commissure locating system allows positioning of the tissue anchor in a position similar to the Kaye Annuloplasty surgical procedure.

The mitral commissure locating system (50) disclosed herein is useful for delivering positioning wires and tissue anchors across the mitral annulus (16) at the mitral commissure and plicating the mitral annulus without potentially being caught by the tendinous chords during the process. One skilled in the art will further recognize that the present teachings could be used to reshape the tricuspid annulus or other heart valve annulus.

Although the present teachings disclose deployments of tissue anchors over a wire place across the mitral annulus, one skilled the in art should understand that tissue anchors can also be delivered with a tissue anchor delivery catheter tracking along the bow wires of the mitral valve commissure locating system as disclosed above. Thus, the specific step of the tissue anchor deployment is subject to change as needed by a person with ordinary skill in the field. Specific embodiments disclosed in the present teachings should not be viewed as limiting.

Various embodiments have been illustrated and described herein by way of examples, and one of ordinary skill in the art will appreciate that variations can be made without departing from the spirit and scope of the present teachings. The present teachings are capable of other embodiments or of being practiced or carried out in various other ways, for example in combinations. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong, Methods and materials similar or equivalent to those described herein can be used in the practice or testing of the present teachings. In case of conflict, the patent specification, including definitions, will control. In addition, the materials, methods, and examples are illustrative only and not intended to be limiting.

The invention claimed is:

1. A method for use at a mitral valve of a heart of a subject, the method comprising:
transluminally advancing a system into the heart;
positioning a first portion of the system through the mitral valve, the system including wires disposed at the first portion;
stabilizing the first portion at the mitral valve by positioning a distal portion of the system within a pulmonary vein of the subject;
while the distal portion of the system remains within the pulmonary vein, inducing the wires to bow laterally such that the wires press against the mitral valve;
while the wires remain pressed against the mitral valve, radiographically imaging a shape of the wires; and
transluminally anchoring an anchor to tissue of the mitral valve, facilitated by the imaging.

2. The method according to claim 1, wherein, for each of the wires, a first segment of the wire is disposed at the first portion and a second segment of the wire is disposed at the distal portion, and wherein inducing the wires to bow laterally comprises inducing the wires to bow laterally such that the second segment of each of the wires moves laterally and secures the distal portion inside the pulmonary vein.

3. The method according to claim 1, wherein:
the wires are first wires,
the system includes second wires disposed at the distal portion, and
positioning the distal portion within the pulmonary vein comprises positioning the second wires within the pulmonary vein.

4. The method according to claim 3, wherein the method further includes securing the distal portion inside the pulmonary vein by inducing the second wires to bow laterally within the pulmonary vein.

5. The method according to claim 1, wherein inducing the wires to bow laterally such that the wires press against the mitral valve comprises inducing the wires to bow laterally such that the wires press against commissures of the mitral valve.

6. The method according to claim 1, wherein the system includes exactly two wires, and wherein inducing the wires to bow laterally such that the wires press against the mitral valve comprises inducing the exactly two wires to bow laterally such that the exactly two wires press against the mitral valve.

7. The method according to claim 1, wherein:
the system includes a bow catheter, and a central catheter that is slidably disposed within a lumen of the bow catheter,
each of the wires has a first end attached to the bow catheter, and a second end attached to the central catheter, and
inducing the wires to bow laterally comprises inducing the wires to bow laterally by sliding the central catheter with respect to the bow catheter.

8. The method according to claim 7, wherein positioning the first portion of the system through the mitral valve comprises positioning the first portion of the system such that the first end of each of the wires is disposed downstream of the mitral valve, and the second end of each of the wires is disposed upstream of the mitral valve.

9. The method according to claim 7, wherein inducing the wires to bow laterally by sliding the central catheter with respect to the bow catheter comprises inducing the wires to bow laterally by retracting the central catheter into the bow catheter.

10. The method according to claim 1, further comprising transluminally advancing a delivery catheter to the heart, and delivering the anchor to the mitral valve via the delivery catheter.

11. The method according to claim 10, further comprising tracking the delivery catheter along one of the wires.

12. The method according to claim 1, wherein anchoring the anchor comprises anchoring the anchor at a posteromedial commissure of the mitral valve.

13. The method according to claim 1, wherein anchoring the anchor comprises anchoring the anchor at an anterolateral commissure of the mitral valve.

14. The method according to claim 1, wherein the anchor is a first anchor, and wherein the method further comprises transluminally anchoring a second anchor to tissue of the mitral valve, facilitated by the imaging.

15. The method according to claim 14, wherein anchoring the first anchor comprises anchoring the first anchor at an anterolateral commissure of the mitral valve, and wherein anchoring the second anchor comprises anchoring the second anchor at a posteromedial commissure of the mitral valve.

16. The method according to claim 14, further comprising, subsequently to anchoring the first and second anchors, transluminally reducing a distance between the first and second anchors by applying tension to a tensile member that is coupled to the first and second anchors.

17. The method according to claim 16, further comprising locking the tension in the tensile member by locking a locker to the tensile member.

18. The method according to claim 17, further comprising, prior to locking the locker to the tensile member, advancing the locker along the tensile member toward the first and second anchors.

19. The method according to claim 17, further comprising, subsequently to locking the locker to the tensile member, using a cutter to remove excess of the tensile member.

20. The method according to claim 1, wherein the system includes a catheter, the wires disposed laterally from the catheter, and wherein positioning the first portion of the system through the mitral valve comprises positioning the system such that the catheter extends through the mitral valve.

21. The method according to claim 1, wherein inducing the wires to bow laterally such that the wires press against the mitral valve comprises inducing the wires to bow laterally until the wires form a waist at the mitral valve.

22. The method according to claim 1, wherein the pulmonary vein is a left pulmonary vein of the subject, and wherein positioning the distal portion within the pulmonary vein comprises positioning the distal portion within the left pulmonary vein.

23. A method for use at a native valve of a heart of a subject, the method comprising:
transluminally advancing a system into the heart;
positioning a first portion of the system through the native valve, the system including wires disposed at the first portion;
stabilizing the first portion at the native valve by positioning a distal portion of the system within a blood vessel of the subject;
while the distal portion of the system remains within the blood vessel, inducing the wires to bow laterally such that the wires press against the native valve;
while the wires remain pressed against the native valve, radiographically imaging a shape of the wires; and
transluminally anchoring an anchor to tissue of the native valve, facilitated by the imaging.

24. The method according to claim 23, wherein, for each of the wires, a first segment of the wire is disposed at the first portion and a second segment of the wire is disposed at the distal portion, and wherein inducing the wires to bow laterally comprises inducing the wires to bow laterally such that the second segment of each of the wires moves laterally and secures the distal portion inside the blood vessel.

25. The method according to claim 23, wherein:
the wires are first wires,
the system includes second wires disposed at the distal portion,
positioning the distal portion within the blood vessel comprises positioning the second wires within the blood vessel, and
the method further comprises securing the distal portion inside the blood vessel by inducing the second wires to bow laterally within the blood vessel.

26. The method according to claim 23, wherein inducing the wires to bow laterally such that the wires press against the native valve comprises inducing the wires to bow laterally such that the wires press against commissures of the native valve.

27. The method according to claim 23, wherein the system includes exactly two wires, and wherein inducing the wires to bow laterally such that the wires press against the native valve comprises inducing the exactly two wires to bow laterally such that the exactly two wires press against the native valve.

28. The method according to claim 23, wherein the anchor is a first anchor, and wherein the method further comprises transluminally anchoring a second anchor to tissue of the native valve, facilitated by the imaging.

29. The method according to claim 23, further comprising, subsequently to anchoring the first and second anchors, transluminally reducing a distance between the first and second anchors by applying tension to a tensile member that is coupled to the first and second anchors.

30. The method according to claim 29, further comprising locking the tension in the tensile member by locking a locker to the tensile member.

31. The method according to claim 30, further comprising, prior to locking the locker to the tensile member, advancing the locker along the tensile member toward the first and second anchors, and subsequently to locking the locker to the tensile member, using a cutter to remove excess of the tensile member.

* * * * *